US005702936A

United States Patent [19]
Beavo et al.

[11] Patent Number: 5,702,936
[45] Date of Patent: Dec. 30, 1997

[54] CYCLIC GMP-BINDING, CYCLIC GMP-SPECIFIC PHOSPHODIESTERASE MATERIALS AND METHODS

[75] Inventors: Joseph A. Beavo, Seattle, Wash.; Jackie D. Corbin, Nashville, Tenn.; Kenneth M. Ferguson, Bothell, Wash.; Sharron H. Francis, Nashville, Tenn.; Ann Kadlecek; Kate Loughney, both of Seattle, Wash.; Linda M. McAllister-Lucas, Nashville, Tenn.; William K. Sonnenburg, Mountlake Terrace, Wash.; Melissa K. Thomas, Boston, Mass.

[73] Assignees: ICOS Corporation, Bothell, Wash.; Vanderbilt University, Nashville, Tenn.; Board of Regents of the University of Washington, Seattle, Wash.

[21] Appl. No.: 250,847

[22] Filed: May 27, 1994

Related U.S. Application Data

[63] Continuation-in-part of Ser. No. 68,051, May 27, 1993, abandoned.

[51] Int. Cl.$^6$ .............................. C12N 9/16; C12N 15/55
[52] U.S. Cl. .................. 435/196; 435/69.1; 435/172.3; 435/320.1; 435/252.3; 435/325
[58] Field of Search ........................... 435/196, 69.1, 435/172.3, 320.1, 252.3, 240.2, 325; 536/23.2

[56] References Cited

FOREIGN PATENT DOCUMENTS

WO 92/18541  10/1992  WIPO.
WO 93/05182  3/1993  WIPO.

OTHER PUBLICATIONS

Ausubel et al., *Current Protocols in Molecular Biology*, John Wiley & Sons, New York (1987) [Table Contents].
Beavo et al., *Cyclic Nucleotide Phosphodiesterases: Structure, Regulation and Drug Action*, John Wiley & Sons, Chichester, UK (1990) [Table of Contents].
Bradford, "A Rapid and Sensitive Method for the Quantitation of Microgram Quantities of Protein Utilizing the Principle of Protein-Dye Binding", *Anal. Biochem.*, 72:248–254 (1976).
Charbonneau et al., "Identification of a Noncatalytic cGMP-Binding Domain Conserved in Both the cGMP--Stimulated and Photoreceptor Cyclic Nucleotide Phosphodiesterases", *Proc. Natl. Acad. Sci. USA*, 87:288–292 (1990).
Charbonneau, "Structure–Function Relationships Among Cyclic Nucleotide Phosphodiesterases", Chapter 11, pp. 267–296 in Beavo et al., *Cyclic Nucleotide Phosphodiesterases: Structure, Regulation and Drug Action*, John Wiley & Sons, Chichester, UK (1990).
Colbran et al., "Cyclic Nucleotide Phosphodiesterases Are Zinc Hydrolases as Indicated by Conserved Zinc–Binding Motifs, Specific Zinc Binding, and Zinc–Supported Catalysis", *The FASEB J.*, 8: Abstract 2148 (Mar. 15, 1994).

Colbran et al., "Mutagenesis of a Lung cGMP-Specific Phosphodiesterase Provides Evidence for Two Distinct Sites for Allosteric cGMP-Binding, with an Essential Aspartic Acid at Each Site", *The FASEB J.*, 8: Abstract 2149 (May 15, 1994).
Collins et al., "The Human β–Subunit of Rod Photoreceptor cGMP Phosphodiesterase:Complete Retinal cDNA Sequence and Evidence for Expression in Brain", *Genomics*, 13:698–704 (1992).
Coquil et al., "Characteristics of a New Binding Protein Distinct From the Kinase for Guanosine 3':5'–Monophosphate in Rat Platelets", *Biochim. Biophys. Acta*, 631:148–165 (1980).
Coquil et al., "Occurrence of the Methylisobutylxanthine–Stimulated Cyclic GMP Binding Protein in Various Rat Tissues", *Biochem. Biophys. Res. Commun.*, 127:226–231 (1985).
Davis et al., "Purification and Characterization of Guanosine 3':5'–Monophosphate-specific Phosphodiesterase from Guinea Pig Lung", *J. Biol. Chem.*, 252:4078–4084 (1977).
Dayhoff et al., "Establishing Homologies in Protein Sequences", *Methods Enzymol.*, 92:524–545 (1983).
Erickson et al., "Macromolecular X–Ray Crystallography and NMR as Tools for Structure–based Drug Design", *Ann. Rep. Med. Chem.*, 27:271–289 (1992).
Feinberg et al., "A Technique for Radiolabeling DNA Restriction Endonuclease Fragments to High Specific Activity", *Anal. Biochem.*, 137:266–267 (1984).
Feng et al., "Progressive Alignment and Phylogenetic Tree Construction of Protein Sequences", *Methods Enzymol.*, 183:375–387 (1990).
Flockhart et al., "Preparation of the Catalytic Subunit of cAMP–Dependent Protein Kinase", Chapter 12, pp. 209–215 in Marangos et al., *Brain Receptor Methodologies*, Part A, Academic Press, Orlando, Florida (1984).
Francis et al., "Cyclic GMP–Binding Cyclic GMP–Specific Phosphodiesterase fron Lung", Chapter 5, pp. 117–140 in Beavo et al., *Cyclic Nucleotide Phosphodiesterases: Structure, Regulation and Drug Action*, John Wiley & Sons, Chicehester, UK (1990).
Francis et al., "Characterization of a Novel cGMP Binding Protein from Rat Lung", *J. Biol. Chem.*, 255:620–626 (1979).
Francis et al., "Purification of cGMP–Binding Protein Phosphodiesterase from Rat Lung", *Methods Enzymol.*, 159:722–729 (1988).

(List continued on next page.)

Primary Examiner—Rebecca E. Prouty
Attorney, Agent, or Firm—Marshall, O'Toole, Gerstein, Murray & Borun

[57] ABSTRACT

The present invention provides novel purified and isolated nucleotide sequences encoding the cGMP-binding, cGMP-specific phosphodiesterase designated cGB-PDE. Also provided by the invention are methods and materials for the recombinant production of cGB-PDE polypeptide products and methods for identifying compounds which modulate the enzymatic activity of cGB-PDE polypeptides.

3 Claims, 10 Drawing Sheets

OTHER PUBLICATIONS

Hamet et al., "Cyclic GMP Binding and Phosphodiesterase-:Implication for Platelet Function", *Adv. Cyclic Nucleotide Protein Phosphorylation Res.*, 16:119–136 (1984).

LeTrong et al., "Amino Acid Sequence of the Cyclic GMP Stimulated Cyclic Nucleotide Phosphodiesterase from Bovine Heart", *Biochemistry*, 29:10280–10288 (1990).

Li et al., "Bovine Cone Photoreceptor cGMP Phosphodiesterase Structure Deduced from A cDNA Clone", *Proc. Natl. Acad. Sci. USA*, 87:293–297 (1990).

Lipkin et al., "β–Subunit of Bovine Rod Photoreceptor cGMP Phosphodiesterase", *J. Biol. Chem.*, 265:12955–12959 (1990).

Martins et al., "Purification and Characterization of a Cyclic GMP–Stimulated Cyclic Nucleotide Phosphodiesterase from Bovine Tissues", *J. Biol. Chem.*, 257:1973–1979 (1982).

Matsudaira, "Sequence from Picomole Quantities of Proteins Electroblotted Onto Polyvinylidene Difluoride Membranes", *J. Biol. Chem.*, 262:10035–10038 (1987).

Murray et al., "Inhibitors of Cyclic Nucleotide Phosphodiesterases as Therapuetic Agents", *Biochem. Soc. Trans.*, 20(2):460–464 (1992).

Oskenberg et al., "A Single Amino–Acid Difference Confers Major Pharmacological Variation Between Human and Rodent 5–$HT_{1B}$ Receptors", *Nature*, 360:161–163 (1992).

Ovchinnikov et al., "Cyclic GMP Phosphodiesterase From Cattle Retina", *FEBS Lett.*, 204:288–292 (1986).

Ovchinnikov et al., "Cyclic GMP Phosphodiesterase from Bovine Retina", *FEBS Lett.*, 223:169–173 (1987).

Price et al., "Expression of Heterologous Proteins in *Saccharomyces cerevisiae* Using the ADH2 Promoter", *Meth. Enzymol.*, 185:308–318 (1990).

Prpic et al., "Separation and Assay of Phosphodiesterase Isoforms in Murine Peritoneal Macrophages Using Membrane Matrix DEAE Chromatography and [$^{32}$P]cAMP", *Anal. Biochem.*, 208:155–160 (1993).

Reeves et al., "Cardiac Phosphodiesterases and the Functional Effects of Selective Inhibition", Chapter 12, pp. 300–316 in Beavo et al., *Cyclic Nucleotide Phosphodiesterases: Structure, Regulation and Drug Action*, John Wiley & Sons, Chichester, UK (1990).

Sonnenburg et al., "Molecular Cloning of a Cyclic GMP–Stimulated Cyclic Nucleotide Phosphodiesterase cDNA", *J. Biol. Chem.*, 266:17655–17661 (1991).

Thomas et al., "Substrate– and Kinase–directed Regulation of Phosphorylation of a cGMP–binding Phosphodiesterase by cGMP", *J. Biol. Chem.*, 265:14971–14978 (1990).

Thomas et al., "Characterization of a Purified Bovine Lung cGMP–Binding cGMP Phosphodiesterase", *J. Biol. Chem.*, 265:14964–14970 (1990).

Vallee and Auld, "Zinc Coordination, Function, and Structure of Zinc Enzymes and Other Proteins", *Biochem.*, 29:5647–5659 (1990).

Wilbur et al., "Rapid Similarity Searches of Nucleic Acid and Protein Data Banks", *Proc. Natl. Acad. Sci. USA*, 80:726–730 (1983).

L.B. Cieslinski et al., "Cyclic Nucleotide Phosphodiesterases (PDEs) in Canine and Human Tracheal Smooth Muscle", FASEB J. 2(5) A 1065, Abst. 4474 (Mar. 1988).

L.M. McAllister–Lucas et al., 'The Structure of a Bovine Lung cGMP–Binding, cGMP–Specific Phosphodiestera Deduced From a cDNA Clone', J. Biol. Chem. 268(30) 22863–22873 (Oct. 1993).

| | | | | | |
|---|---|---|---|---|---|
| cGB-PDE | FQMKHEVLCK | WILSVKKNYR | K.NVAYHNWR | HAFNTAQCMF | AALKAGKIQK | 626 |
| ROS-α | FHIPQEALVR | FMYSLSKGYR | R..ITYHNWR | HGFNVGQTMF | SLLVTGKLKR | 582 |
| ROS-β | FQIPQEVLVR | FLFSVSKGYR | R..ITYHNWR | HGFNVAQTMF | TLLMTGKLKS | 580 |
| CONE-α' | FKVPVEVLTR | WMTYVRKGYR | A..VTYHNWR | HGFNVGQTMF | TLLMTGRLKK | 580 |
| cGS | YKIDCPTLAR | FCLMVKKGYR | D.P.PYHNWM | HAFSVSHFCY | LLYKNLELTN | 659 |
| 61 KCaM | FKIPVSCLIA | FAEALEVGYS | KYKNPYHNLI | HAADVTQTVH | YIMLHTGIMH | 242 |
| 63 KCaM | FKIPTVFLMT | FLDALETGYG | KYKNPYHNQI | HAADVTQTVH | CFLLRTGMVH | 244 |
| Ratdunce | FQIPADTLLR | YLLTLEGHYH | S.NVAYHNSI | HAADVVQSAH | VLLGTPALEA | 125 |
| Drosdunce | .MIPPKTFLN | FMSTLEDHYV | K.DNPFHNSL | HAADVTQSTN | VLLNTPALEG | 48 |
| Conserved | -----*--- | -------- | -----HN-* | H-------- | -----*---- | |
| cGB-PDE | RLTDLEILAL | LIAALSHDLD | HRGVNNSYIQ | RSEHPLAQLY | CH..SIMEHH | 674 |
| ROS-α | YFTDLEALAM | VTAAFCHDID | HRGTNNLYQM | KSQNPLAKLH | GS..SILERH | 630 |
| ROS-β | YYTDLEAFAM | VTAGLCHDID | HRGTNNLYQM | KSQNPLAKLH | GS..SILERH | 628 |
| CONE-α' | YYTDLEAFAM | LAAAFCHDID | HRGTNNLYQM | KSTSPLARLH | GS..SILERH | 628 |
| cGS | YLEDMEIFAL | FISCMCHDLD | HRGTNNSFQV | ASKSVLAALY | SSEGSVMERH | 709 |
| 61 KCaM | WLTELEILAM | VFAAAIHDYE | HIGTTNNFHI | QTRSDVAILY | .NDRSVLENH | 291 |
| 63 KCaM | CLSEIEVLAI | IFAAAIHDYE | HIGTTNSFHI | QTKSEQAILY | .NDRSVLENH | 293 |
| Ratdunce | VFTDLEVLAA | IFACAIHDVD | HPGVSNQFLI | NTNSELALMY | .NDSSVLENH | 174 |
| Drosdunce | VFTPLEVGGA | LFAACIHDVD | HPGLTNQFLV | NSSSELALMY | .NDESVLENH | 97 |
| Conserved | ----E---- | -----HD-- | H-G---N-*- | ---*-A--- | ----S--E-H | |

FIGURE 1A

| | | | | | | |
|---|---|---|---|---|---|---|
| cGB-PDE | HFDQCLMILN | SPGNQILSGL | SIEEYKTTLK | IIKQAILATD | LALYIKRRGE | 724 |
| ROS-α | HLEFGKTLLR | DESLNIFQNL | NRRQHEHAIH | MMDIAIIATD | LALYCKKRTM | 680 |
| ROS-β | HLEFGKFLLS | EETLNIYQNL | NRRQHEHVIH | LMDIAIIATD | LALYFKKRTM | 678 |
| CONE-α' | HLEYSKTLLQ | DESLNIFQNL | NKRQYETVIH | LFEVAIIATD | LALYFKKRTM | 678 |
| CGS | HFAQAIAILN | THGCNIFDHF | SRKDYQRMLD | LMRDIILATD | LAHHLRIFKD | 748 |
| 61 kCaM | HVSAAYRLMQ | EEEMNVLINL | SKDDWRDLRN | LVIEMVLSTD | MSGHFQQIKN | 326 |
| 63 kCaM | HISSVFRMMQ | DDEMNIFINL | TKDEFVELRA | LVIEMVLATD | MSCHFQQVKS | 328 |
| Ratdunce | HLAVGFKLLQ | GENCDIFQNL | STKQKLSLRR | MVIDMVLATD | MSKHMSLLAD | 220 |
| Drosdunce | HLAVAFKLLQ | NQGCDIFCNM | QKKQRQTLRK | MVIDIVLSTD | MSKHMSLLAD | 143 |
| Conserved | H--------- | ---------- | ---------- | -------TD | --*--*---- | |

| | | | | | | |
|---|---|---|---|---|---|---|
| cGB-PDE | FFELIMKN.. | .....QF | NLEDPHQKEL | FLAMLMTACD | LSAITKPWPI | 764 |
| ROS-α | FQKIVDQSKT | YETQQEWTQY | MMLDQTRKEI | VMAMMMTACD | LSAITKPWEV | 730 |
| ROS-β | FQKIVDESKN | YEDRKSWVEY | LSLETTRKEI | VMAMMMTACD | LSAITKPWEV | 728 |
| CONE-α' | FQKIVDACEK | METEEEAIKY | VTIDPTKKEI | IMAMMMTACD | LSAITKPWEV | 728 |
| CGS | LQKWAE.... | ......VGY | DRTNKQHHSL | LCCLLMTSCD | LSDQTKGWKT | 798 |
| 61 kCaM | IRNSLQQPEG | L......... | ......DKAK | TMSLILHAAD | ISHPAKSWKL | 376 |
| 63 kCaM | MKTALQQLER | I......... | ......DKSK | ALSLLLHAAD | ISHPTKQWSV | 378 |
| Ratdunce | LKTMVETKKV | T....SLGVL | LLDNYSDRIQ | VLQSLVHCAD | LSNPAKPLPL | 270 |
| Drosdunce | LKTMVETKKV | A....GSGVL | LLDNYTDRIQ | VLENLVHCAD | LSNPTKPLPL | 193 |
| Conserved | *--------- | ---------- | ---------- | --*------- | -S**-K---- | |

FIGURE 1B

| | | | | | |
|---|---|---|---|---|---|
| CGB-PDE | QQRIAELVAT | EFFDQGDRER | KELNIEPADL | MNREKKNKIP | SMQVGFID.. | 812 |
| ROS-α | QSKVALLVAA | EFWEQGDLER | TVLQQNPIPM | MDRNKADELP | KLQVGFID.. | 778 |
| ROS-β | QSKVALLVAA | EFWEQGDLER | TVLDQQPIPM | MDRNKAAELP | KLQVGFID.. | 776 |
| CONE-α' | QSQVALLVAN | EFWEQGDLER | TVLQQQPIPM | MDRNKKDELP | KLQVGFID.. | 776 |
| CGS | TRKIAELIYK | EFFSQGDLEK | A..MGNRPMEM | MDREKAY.IP | ELQISFME.. | 844 |
| 61 KCAM | HHRWTMALME | EFFLQGDKEA | EL..GLPFSP | LCDRKSTMVA | QSQIGFID.. | 422 |
| 63 KCAM | HSRWTKALME | EFFRQGDKEA | EL..GLPFSP | LCDRTSTLVA | QSQIGFID.. | 424 |
| Ratdunce | YRQWTERIMA | EFFQQGDRER | ES..GLDISP | MCDKHTASVE | KSQVGFID.. | 316 |
| Drosdunce | YKRWVALLME | EFFLQGDKER | ES..GMDISP | MCDRHNATIE | KSQVGFID.. | 239 |
| Conserved | *-----**- | EF--QGD-E- | ---------- | ---------- | --Q--F--- | |

FIGURE 1C

```
cGB-PDE    LLELVKDISS  HLDVTALCHK   IFLHIHGLIS   ADRYSLFLVC   EDSSNDKFLI   188
CGS        ILQLCGELYD  .LDASSLQLK   VLQYLQQETQ   ASRCCLLLVS   EDN..LQ.LS   245
CONE-α'    LLEVL..LEE  AGSVELAAHR   ALQRLAQLLQ   ADRCSMFLCR   ARNGTPE.VA   106
ROS-β      LFELVQDMQE  NVNMERVVFK   ILRRLCSILH   ADRCSLFMYR   QRNGVAE.LA   107
ROS-α      ...LLRDFQD  NLQAEKCVFN   VMKKLCFLLQ   ADRMSLFMYR   ARNGIAE.LA   109
CONSERVED  ---------   ----------   ----------   A-R-------   ---------- cGB-PDE    SRLFDVAEGS  TLEE...ASN   NCIRLEWNKG   IVGHVAAFGE   PLNIKDAYED   237
CGS        CKVIG..DK   VLEE......   .EISFPLTTG   RLGQVVEDKK   SIQLKDLTSE   292
CONE-α'    SKLLDVTPTS  KFEDNLVVPD   REAVFPLDVG   IVGWVAHTKK   TFNVPDVKKN   154
ROS-β      TRLFSVQPDS  VLEDCLVPPD   SEIVFPLDIG   VVGHVAQTKK   MVNVQDVMEC   155
ROS-α      TRLFNVHKDA  VLEECLVAPD   SEIVFPLDMG   VVGHVALSKK   IVNVPNTEED   157
CONSERVED  ---------   ----------   ----------   --G--V----   ---------- cGB-PDE    PRFNAEVDQI  TGYKTQSILC   MPIKNHR.EE   VVGVAQAINK   KSGNGGTFTE   287
CGS        DM..QQLQSM  LGCEVQAMLC   VPVISRATDQ   VVALACAFNK   ..LGGDLFTD   342
CONE-α'    SHFSDFMDKQ  TGYVTRNLLA   TPIV..MGKE   VLAVFMAVNK   ..VDASEFSK   204
ROS-β      PHFSSFADEL  TDYYTRNILA   TPIM..NGKD   VVAVIMAVNK   ..LDGPCFTS   205
ROS-α      EHFCDFVDTL  TEYQTKNILA   SPIM..NGKD   VVAIIMAVNK   ..VDGPHFTE   207
CONSERVED  ---------   ----------   --P-------   V----A-NK    ----F-----
```

```
CGB-PDE      KDEKDFAAYL AFCGIVLHNA QLYETSLLEN KRNQVLLDLA SLIFEEQQSL   337
CGS          QDEHVIQHCF HYTSTVLTST LAFQKEQKLK CECQALLQVA KNLFTHLDDV   390
CONE-α'      QDEEVFSKYL SFVSIILKLH HTNYLYNIES RRSQILMWSA NKVFEELTDV   252
ROS-β        EDEDVFLKYL NFGTLNLKIY HYSYLHNCET RRGQVLLWSA NKVFEELTDI   253
ROS-α        NDEEILLKYL NFANLIMKVF HLSYLHNCET RRGQILLWSG SKVFEELTDI   255
CONSERVED    -DE------- ---------- ---------- ---Q--L--- ---F------

CGB-PDE      EVILKKIAAT IISFMQVQKC TIFIVD.EDC SDSFSSVFHM ECEELEKSSD   386
CGS          SVLLQEITTE ARNLSNAEIC SVFLID...Q NELVAKVFDG GVLEDESY..   409
CONE-α'      ERQFHKALYT VRTYLNCERY SIGLLDMTKE KEFY.DEWPV KPGEVEPYKG   301
ROS-β        ERQFHKAFYT VRAYLNCDRY SVGLLDMTKE KEFF.DVWPV LMGEAQAYSG   302
ROS-α        ERQFHKALYT VRAFLNCDRY SVGLLDMTKQ KEFF.DVWPV LMGEAPPYAG   304
CONSERVED    ---------- ---------- ----D----- ---------- ----E-----

CGB-PDE      TLTRE..... .......... .....EIRI. .RDANRINY MYAQYVKNTM    409
CGS          PKTPDGREVI FYKIIDYILH GKEEIKVIPT .PADQ..... GIAGHVATTG    459
CONE-α'      PRTPDGREIL FYKVIDYILH GKEDIKVIPS PPMDHWTLIS GLPTYVAENG    351
ROS-β        PRTPDGREIL FYKVIDYILH GKEDIKVIPS PPADHWALAS GLPTYVAESG    352
ROS-α        PRTPDGREIN FYKVIDYILH GKEDIKVIPN PPPDHWALVS GLPTYVAQNG    354
CONSERVED    ---------- ---------- ---------- -----D---- ----V-----
```

```
cGB-PDE     EPLNIPDVSK  DKRFPWTNEN  MGNINQQCIR  SLLCTPIKNG  KKNKVIGVCQ  459
cGS         QILNIPDAYA  HPLFY..RGV  DDSTGRF.TR  NILCFPIKN.  ENQEVIGVAE  499
CONE-α'     FICNMLNAPA  DEYFTFQKGP  VDETGWV.IK  NVLSLPIVN.  KKEDIVGVAT  399
ROS-β       FICNIMNAPA  DEMFNFQEGP  LDDSGWI.VK  NVLSMPIVN.  KKEEIVGVAT  400
ROS-α       LICNIMNAPS  EDFFAFQKEP  LDESGWM.IK  NVLSMPIVN.  KKEEIVGVAT  402
CONSERVED   ---N------  ---F------  ----------  --L--PI-N-  -----GV--- cGB-PDE     LVNKMEETTG  KVKAFNRNDE  QFLEAFVIFC  GLGIQNTQMY  EAVERAMAKQ  509
cGS         LVNKING...  .PWFSKFDE   DLATAFSIYC  GISIAHSLLY  KKVNEAQYRS  541
CONE-α'     FYNRKDG...  ..KPFDEYDE  HIAETLTQFL  GWSLLNTDTY  EKMNKLENRK  441
ROS-β       FYNRKDG...  ..KPFDEQDE  VLMESLTQFL  GWSVLNTDTY  DKMNKLENRK  442
ROS-α       FYNRKDG...  ..KPFDEMDE  TLMESLAQFL  GWSVLNPDTY  ELMNKLENRK  444
CONSERVED   ---N------  ---F----DE  ----------  -G--------  -Y-------- cGB-PDE     MVTLEVLSYH  ASAAEEE                                         526
cGS         HLANEMMYH   MKVSDDE                                         561
CONE-α'     DIAQEMLMNH  TKATPDE                                         461
ROS-β       DIAQDMVLYH  VRCDREE                                         462
ROS-α       DIFQDMVKYH  VKCDNEE                                         464
CONSERVED   --------H   -----E
```

| | | |
|---|---|---|
| cGB-PDE | A | EPLNIKDAYEDPRF...NAEVDQITGYKTQSILCMPIKMH.REEVVGVAQAIN.KKSGN |
| ROS-α | A | KIVNVPNTEEDEHF...CDFVDTLTEYQTKNILASPIMNG.K.DVVAIIMAVN.KVDGP |
| ROS-β | A | KMVNVQDVMECPHF...SSFADELTDYVTRNILATPIMNG.K.DVVAVIMAVN.KLDGP |
| CONE-α' | A | KTFNVPDVKKNSHF...SDFMDKQTGYVTRNILATPIVMG.K.EVLAVFMAVN.KVDAS |
| CGS | | KSIQLKDLTSEDM......QQLQSMLGCEVQAMLCVPVISRATDQVVALACAFN.KLGGD |
| cGB-PDE | B | EPLNIPDVSKDKRFPWTNENMGNINQCIRSLLCTPIKNGKNKVIGVCQLVN.KMEET |
| ROS-α | B | LICNIMNAPSEDFFAFQKEPLDE.SGMMIKNVLSMPIVNK.KEEIVGVATFYNRKDGKP |
| ROS-β | B | FICNIMNAPADEMFNFOEGPLDD.SGWIVKNVLSMPIVNK.KEEIVGVATFYNRKDGKP |
| CONE-α' | B | FICMLNAPADEYFTFQKGPVDE.TGWVIKNVSLPIVNK.KEDIVGVATFYNRKDGKP |
| CGS | B | QILNIPDAYAHPLF...YRGVDDSTGFRTRNILCFPIKNE.NQEVIGVAELVN.KINGP |
| CONSERVED | | ---*---*-----------------L-.P*----------*-----N-K---- |

| | | |
|---|---|---|
| cGB-PDE | A | GG....TFTEKDEKDFAAYLAFCGIVLHMAQL.YE |
| ROS-α | A | .....HFTENDEEILLKYLNFANLIMKVFHLSY. |
| ROS-β | A | .....CFTSEDEDEVFLKYLNFGTLNLKIYHLSY. |
| CONE-α' | A | .....EFSKQDEEVFSKYLSFVSIILKLHHTNY. |
| CGS | | .....LFTDQDEHVIQHCFHYTSTVL.TSTLAFQ |
| cGB-PDE | B | TGKVKAFNRNDEQFLEAFVIFCGLGIQNTOM.YE |
| ROS-α | B | .....FDEMDETLMESLAQFLGWSV.LNPDTYE |
| ROS-β | B | .....FVEQDEVLMESLTQFLGWSV.LNTDTYD |
| CONE-α' | B | .....FDEYDEHIAETLTQFLGWSL.LNTDTYE |
| CGS | B | .....WFSKFDEDLATAFSIYCGISI.AHSLLYK |
| CONSERVED | | ----F----DE--------------*------ |

CYCLIC GMP-BINDING, CYCLIC GMP-SPECIFIC PHOSPHODIESTERASE MATERIALS AND METHODS

This application is a continuation-in-part of U.S. patent application Ser. No. 08/068,051 filed May 27, 1993, now abandoned.

Experimental work described herein was supported in part by Research Grants GM15731, DK21723, DK40029 and GM41269 and the Medical Scientist Training Program Grant GM07347 awarded by the National Institutes of Health. The United States government has certain rights in the invention.

FIELD OF THE INVENTION

The present invention relates generally to a cyclic guanosine monophosphate-binding, cyclic guanosine monophosphate-specific phosphodiesterase designated cGB-PDE and more particularly to novel purified and isolated polynucleotides encoding cGB-PDE polypeptides, to methods and materials for recombinant production of cGB-PDE polypeptides, and to methods for identifying modulators of cGB-PDE activity.

BACKGROUND

Cyclic nucleotide phosphodiesterases (PDEs) that catalyze the hydrolysis of 3'5' cyclic nucleotides such as cyclic guanosine monophosphate (cGMP) and cyclic adenosine monophosphate (cAMP) to the corresponding nucleoside 5' monophosphates constitute a complex family of enzymes. By mediating the intracellular concentration of the cyclic nucleotides, the PDE isoenzymes function in signal transduction pathways involving cyclic nucleotide second messengers.

A variety of PDEs have been isolated from different tissue sources and many of the PDEs characterized to date exhibit differences in biological properties including physicochemical properties, substrate specificity, sensitivity to inhibitors, immunological reactivity and mode of regulation. [See Beavo et al., *Cyclic Nucleotide Phosphodiesterases: Structure, Regulation and Drug Action*, John Wiley & Sons, Chichester, U.K. (1990)] Comparison of the known amino acid sequences of various PDEs indicates that most PDEs are chimeric multidomain proteins that have distinct catalytic and regulatory domains. [See Charbonneau, pp. 267–296 in Beavo et al., supra] All mammalian PDEs characterized to date share a sequence of approximately 250 amino acid residues in length that appears to comprise the catalytic site and is located in the carboxyl terminal region of the enzyme. PDE domains that interact with allosteric or regulatory molecules are thought to be located within the amino-terminal regions of the isoenzymes. Based on their biological properties, the PDEs may be classified into six general families: the $Ca^{2+}$/calmodulin-stimulated PDEs (Type I), the cGMP-stimulated PDEs (Type II), the cGMP-inhibited PDEs (Type III), the cAMP-specific PDEs (Type IV), the cGMP-specific phosphodiesterase cGB-PDE (Type V) which is the subject of the present invention and the cGMP-specific photoreceptor PDEs (Type VI).

The cGMP-binding PDEs (Type II, Type V and Type VI PDEs), in addition to having a homologous catalytic domain near their carboxyl terminus, have a second conserved sequence which is located closer to their amino terminus and which may comprise an allosteric cGMP-binding domain. See Charbonneau et al., *Proc. Natl. Acad. Sci. U.S.A.*, 87:288–292 (1990).

The Type II cGMP-stimulated PDEs (cGs-PDEs) are widely distributed in different tissue types and are thought to exist as homodimers of 100–105 kDa subunits. The cGs-PDEs respond under physiological conditions to elevated cGMP concentrations by increasing the rate of cAMP hydrolysis. The amino acid sequence of a bovine heart cGs-PDE and a partial cDNA sequence of a bovine adrenal cortex cGS-PDE are reported in LeTrong et al., *Biochemistry*, 29:10280–10288 (1990) and full length bovine adrenal and human fetal brain cGB-PDE cDNA sequences are described in Patent Cooperation Treaty International Publication No. WO 92/18541 published on Oct. 29, 1992. The full length bovine adrenal cDNA sequence is also described in Sonnenburg et al., *J. Biol. Chem.*, 266:17655–17661 (1991).

The photoreceptor PDEs and the cGB-PDE have been described as cGMP-specific PDEs because they exhibit a 50-fold or greater selectivity for hydrolyzing cGMP over cAMP.

The photoreceptor PDEs are the rod outer segment PDE (ROS-PDE) and the cone PDE (COS-PDE). The holoenzyme structure of the ROS-PDE consists of two large subunits α (88 kDa) and β (84 kDa) which are both catalytically active and two smaller γ regulatory subunits (both 11 kDa). A soluble form of the ROS-PDE has also been identified which includes α, β, and γ subunits and a δ subunit (15 kDa) that appears to be identical to the COS-PDE 15 kDa subunit. A full-length cDNA corresponding to the bovine membrane-associated ROS-PDE α subunit is described in Ovchinnikov et al, *FEBS Lett.*, 223:169–173 (1987) and a full length cDNA corresponding to the bovine rod outer segment PDE β subunit is described in Lipkin et al., *J. Biol. Chem.*, 265:12955–12959 (1990). Ovchinnikov et al., *FEBS Lett.*, 204:169–173 (1986) presents a full-length cDNA corresponding to the bovine ROS-PDE γ subunit and the amino acid sequence of the δ subunit. Expression of the ROS-PDE has also been reported in brain in Collins et al, *Genomics*, 13:698–704 (1992). The COS-PDE is composed of two identical α' (94 kDa) subunits and three smaller subunits of 11 kDa, 13 kDa and 15 kDa. A full-length cDNA corresponding to the bovine COS-PDE α' subunit is reported in Li et al., *Proc. Natl. Acad. Sci. U.S.A.*, 87:293–297 (1990).

cGB-PDE has been purified to homogeneity from rat [Francis et al., *Methods Enzymol.*, 159:722–729 (1988)] and bovine lung tissue [Thomas et al, *J. Biol. Chem.*, 265:14964–14970 (1990), hereinafter "Thomas I"]. The presence of this or similar enzymes has been reported in a variety of tissues and species including rat and human platelets [Hamet et al., *Adv. Cyclic Nucleotide Protein Phosphorylation Res.*, 16:119–136 (1984)], rat spleen [Coquil et al., *Biochem. Biophys. Res. Commun.*, 127:226–231 (1985)], guinea pig lung [Davis et al., *J. Biol. Chem.*, 252:4078–4084 (1977)], vascular smooth muscle [Coquil et al., *Biochim. Biophys. Acta*, 631:148–165 (1980)], and sea urchin sperm [Francis et al, *J. Biol. Chem.*, 255:620–626 (1979)]. cGB-PDE may be a homodimer comprised of two 93 kDa subunits. [See Thomas I, supra] cGB-PDE has been shown to contain a single site not found in other known cGMP-binding PDEs which is phosphorylated by cGMP-dependent protein kinase (cGK) and, with a lower affinity, by cAMP-dependent protein kinase (cAK). [See Thomas et al, *J. Biol. Chem.*, 265: 14971–14978 (1990), hereinafter "Thomas II"] The primary amino acid sequence of the phosphorylation site and of the amino-terminal end of a fragment generated by chymotryptic digestion of cGB-PDE are described in Thomas II, supra, and Thomas I, supra, respectively. However, the majority of the amino acid sequence of cGB-PDE has not previously been described.

Various inhibitors of different types of PDEs have been described in the literature. Two inhibitors that exhibit some specificity for Type V PDEs are zaprinast and dipyridamole. See Francis et al, pp. 117–140 in Beavo et al, supra.

Elucidation of the DNA and amino acid sequences encoding the cGB-PDE and production of cGB-PDE polypeptide by recombinant methods would provide information and material to allow the identification of novel agents that selectively modulate the activity of the cGB-PDEs. The recognition that there are distinct types or families of PDE isoenzymes and that different tissues express different complements of PDEs has led to an interest in the development of PDE modulators which may have therapeutic indications for disease states that involve signal transduction pathways utilizing cyclic nucleotides as second messengers. Various selective and non-selective inhibitors of PDE activity are discussed in Murray et al., *Biochem. Soc. Trans.*, 20(2): 460–464 (1992). Development of PDE modulators without the ability to produce a specific PDE by recombinant DNA techniques is difficult because all PDEs catalyze the same basic reaction, have overlapping substrate specificities and occur only in trace amounts. As a result, purification to homogeneity of many PDEs is a tedious and difficult process.

There thus continues to exist a need in the art for DNA and amino acid sequence information for the cGB-PDE, for methods and materials for the recombinant production of cGB-PDE polypeptides and for methods for identifying specific modulators of cGB-PDE activity.

SUMMARY OF THE INVENTION

The present invention provides novel purified and isolated polynucleotides (e.g., DNA sequences and RNA transcripts, both sense and antisense strands, including splice variants thereof) encoding the cGMP-binding, cGMP-specific PDE designated cGB-PDE. Preferred DNA sequences of the invention include genomic and cDNA sequences as well as wholly or partially chemically synthesized DNA sequences. DNA sequences encoding cGB-PDE that are set out in SEQ ID NO: 9 or 20 and DNA sequences which hybridize thereto under stringent conditions or DNA sequences which would hybridize thereto but for the redundancy of the genetic code are contemplated by the invention. Also contemplated by the invention are biological replicas (i.e., copies of isolated DNA sequences made in vivo or in vitro) of DNA sequences of the invention. Autonomously replicating recombinant constructions such as plasmid and viral DNA vectors incorporating cGB-PDE sequences and especially vectors wherein DNA encoding cGB-PDE is operatively linked to an endogenous or exogenous expression control DNA sequence and a transcriptional terminator are also provided. Specifically illustrating expression plasmids of the invention is the plasmid hcgbmet156-2 6n in *E. coli* strain JM109 which was deposited with the American Type Culture Collection (ATCC), 12301 Parklawn Drive, Rockville, Md. 20852, on May 4, 1993 as Accession No. 69296.

According to another aspect of the invention, host cells including procaryotic and eucaryotic cells, are stably transformed with DNA sequences of the invention in a manner allowing the desired polypeptides to be expressed therein. Host cells expressing cGB-PDE products can serve a variety of useful purposes. Such cells constitute a valuable source of immunogen for the development of antibody substances specifically immunoreactive with cGB-PDE. Host cells of the invention are conspicuously useful in methods for the large scale production of cGB-PDE polypeptides wherein the cells are grown in a suitable culture medium and the desired polypeptide products are isolated from the cells or from the medium in which the cells are grown by, for example, immunoaffinity purification.

cGB-PDE products may be obtained as isolates from natural cell sources or may be chemically synthesized, but are preferably produced by recombinant procedures involving host cells of the invention. Use of mammalian host cells is expected to provide for such post-translational modifications (e.g., glycosylation, truncation, lipidation and tyrosine, serine or threonine phosphorylation) as may be needed to confer optimal biological activity on recombinant expression products of the invention. cGB-PDE products of the invention may be full length polypeptides, fragments or variants. Variants may comprise cGB-PDE polypeptide analogs wherein one or more of the specified (i.e., naturally encoded) amino acids is deleted or replaced or wherein one or more nonspecified amino acids are added: (1) without loss of one or more of the biological activities or immunological characteristics specific for cGB-PDE; or (2) with specific disablement of a particular biological activity of cGB-PDE.

Also comprehended by the present invention are antibody substances (e.g., monoclonal and polyclonal antibodies, single chain antibodies, chimeric antibodies, CDR-grafted antibodies and the like) and other binding proteins specific for cGB-PDE. Specific binding proteins can be developed using isolated or recombinant cGB-PDE or cGB-PDE variants or cells expressing such products. Binding proteins are useful, in turn, in compositions for immunization as well as for purifying cGB-PDE polypeptides and detection or quantification of cGB-PDE polypeptides in fluid and tissue samples by known immunogical procedures. They are also manifestly useful in modulating (i.e., blocking, inhibiting or stimulating) biochemical activities of cGB-PDE, especially those activities involved in signal transduction. Anti-idiotypic antibodies specific for anti-cGB-PDE antibody substances are also contemplated.

The scientific value of the information contributed through the disclosures of DNA and amino acid sequences of the present invention is manifest. As one series of examples, knowledge of the sequence of a cDNA for cGB-PDE makes possible the isolation by DNA/DNA hybridization of genomic DNA sequences encoding cGB-PDE and specifying cGB-PDE expression control regulatory sequences such as promotors, operators and the like. DNA/DNA hybridization procedures carried out with DNA sequences of the invention under stringent conditions are likewise expected to allow the isolation of DNAs encoding allelic variants of cGB-PDE, other structurally related proteins sharing one or more of the biochemical and/or immunological properties specific to cGB-PDE, and non-human species proteins homologous to cGB-PDE. Polynucleotides of the invention when suitably labelled are useful in hybridization assays to detect the capacity of cells to synthesize cGB-PDE. Polynucleotides of the invention may also be the basis for diagnostic methods useful for identifying a genetic alteration(s) in the cGB-PDE locus that underlies a disease stare or status. Also made available by the invention are anti-sense polynucleotides relevant to regulating expression of cGB-PDE by those cells which ordinarily express the same.

The DNA and amino acid sequence information provided by the present invention also makes possible the systematic analysis of the structure and function of cGB-PDE and definition of those molecules with which it will interact. Agents that modulate cGB-PDE activity may be identified by incubating a putative modulator with lysate from eucaryotic cells expressing recombinant cGB-PDE and determining the effect of the putative modulator on cGB-PDE phosphodiesterase activity. In a preferred embodiment the eucaryotic cell lacks endogenous cyclic nucleotide phosphodiesterase activity. Specifically illustrating such a eucaryotic cell is the yeast strain YKS45 which was deposited with the ATCC on May 19, 1993 as Accession No. 74225. The selectivity of a compound that modulates the activity of the cGB-PDE can be evaluated by comparing its activity on the cGB-PDE to its activity on other PDE isozymes. The combination of the recombinant cGB-PDE products of the invention with other recombinant PDE products in a series of independent assays provides a system for developing selective modulators of cGB-PDE.

Selective modulators may include, for example, antibodies and other proteins or peptides which specifically bind to the cGB-PDE or cGB-PDE nucleic acid, oligonucleotides which specifically bind to the cGB-PDE or cGB-PDE nucleic acid and other non-peptide compounds (e.g., isolated or synthetic organic molecules) which specifically react with cGB-PDE or cGB-PDE nucleic acid. Mutant forms of cGB-PDE which affect the enzymatic activity or cellular localization of the wild-type cGB-PDE are also contemplated by the invention. Presently preferred targets for the development of selective modulators include, for example: (1) the regions of the cGB-PDE which contact other proteins and/or localize the cGB-PDE within a cell, (2) the regions of the cGB-PDE which bind substrate, (3) the allosteric cGMP-binding site(s) of cGB-PDE, (4) the phosphorylation site(s) of cGB-PDE and (5) the regions of the cGB-PDE which are involved in dimerization of cGB-PDE subunits. Modulators of cGB-PDE activity may be therapeutically useful in treatment of a wide range of diseases and physiological conditions.

BRIEF DESCRIPTION OF THE DRAWINGS

Numerous other aspects and advantages of the present invention will be apparent upon consideration of the following detailed description thereof, reference being made to the drawing wherein:

FIGS. 1A to 1C is an alignment of the conserved catalytic domains of several PDE isoenzymes wherein residues which are identical in all PDEs listed are indicated by their one letter amino acid abbreviation in the "conserved" line, residues which are identical in the cGB-PDE and photoreceptor PDEs only are indicated by a star in the "conserved" line and gaps introduced for optimum alignment are indicated by periods;

FIGS. 2A to 2C is an alignment of the cGMP-binding domains of several PDE isoenzymes wherein residues which are identical in all PDEs listed are indicated by their one letter amino acid abbreviation in the "conserved" line and gaps introduced for optimum alignment are indicated by periods;

FIG. 3 is an alignment of internally homologous repeats from several PDE isoenzymes wherein residues identical in each repeat A and B from all cGMP-binding PDEs listed are indicated by their one letter amino acid abbreviation in the "conserved" line and stars in the "conserved" line represent positions in which all residues are chemically conserved;

DETAILED DESCRIPTION

Figure 4:
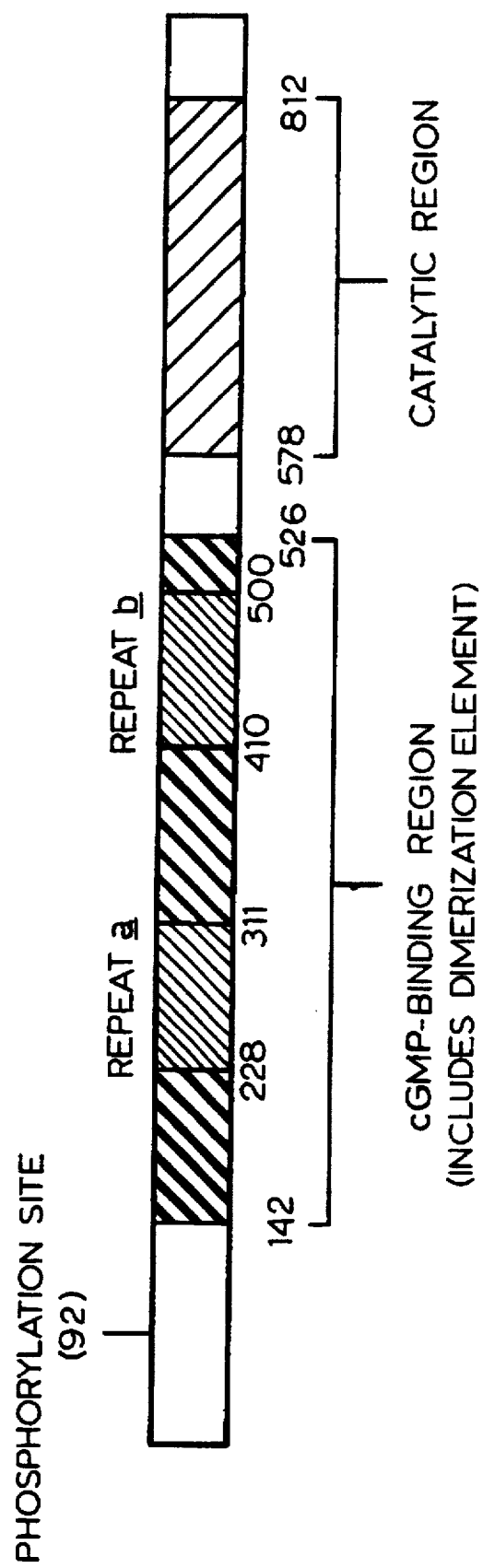
FIG. 4 schematically depicts the domain organization of cGB-PDE.

The following examples illustrate the invention. Example 1 describes the isolation of a bovine cGB-PDE cDNA fragment by PCR and subsequent isolation of a full length cGB-PDE cDNA using the PCR fragment as a probe. Example 2 presents an analysis of the relationship of the bovine cGB-PDE amino acid sequence to sequences reported for various other PDEs. Northern blot analysis of cGB-PDE mRNA in various bovine tissues is presented in Example 3. Expression of the bovine cGB-PDE cDNA in COS cells is described in Example 4. Example 5 presents results of assays of the cGB-PDE COS cell expression product for phosphodiesterase activity, cGMP-binding activity and $Zn^{2+}$ hydrolase activity. Example 6 describes the isolation of human cDNAs homologous to the bovine cGB-PDE cDNA. The expression of a human cGB-PDE cDNA in yeast cells is presented in Example 7. RNase protection assays to detect cGB-PDE in human tissues are described in Example 8. Example 9 describes the bacterial expression of human cGB-PDE cDNA and the development of antibodies reactive with the bacterial cGB-PDE expression product. Example 10 describes cGB-PDE analogs and fragments. The generation of monoclonal antibodies that recognize cGB-PDE is described in Example 11. Example 12 relates to utilizing recombinant cGB-PDE products of the invention to develop agents that selectively modulate the biological activities of cGB-PDE.

EXAMPLE 1

The polymerase chain reaction (PCR) was utilized to isolate a cDNA fragment encoding a portion of cGB-PDE from bovine lung first strand cDNA. Fully degenerate sense and antisense PCR primers were designed based on the partial cGB-PDE amino acid sequence described in Thomas I, supra, and novel partial amino acid sequence information.
A. Purification of cGB-PDE Protein cGB-PDE was purified as described in Thomas I, supra, or by a modification of that method as described below.

Fresh bovine lungs (5–10 kg) were obtained from a slaughterhouse and immediately placed on ice. The tissue was ground and combined with cold PEM buffer (20 mM sodium phosphate, pH 6.8, containing 2 mM EDTA and 25 mM β-mercaptoethanol). After homogenization and centrifugation, the resulting supernatant was incubated with 4–7 liters of DEAE-cellulose (Whatman, UK) for 3–4 hours.

The DEAE slurry was then filtered under vacuum and rinsed with multiple volumes of cold PEM. The resin was poured into a glass column and washed with three to four volumes of PEM. The protein was eluted with 100 mM NaCl in PEM and twelve 1-liter fractions were collected. Fractions were assayed for IBMX-stimulated cGMP binding and cGMP phosphodiesterase activities by standard procedures described in Thomas et al., supra. Appropriate fractions were pooled, diluted 2-fold with cold, deionized water and subjected to Blue Sepharose® CL-6B (Pharmacia LKB Biotechnology Inc., Piscataway, N.J.) chromatography. Zinc chelate affinity adsorbent chromatography was then performed using either an agarose or Sepharose-based gel matrix. The resulting protein pool from the zinc chelation step treated as described in the Thomas I, supra, or was subjected to a modified purification procedure.

As described in Thomas I, supra, the protein pool was applied in multiple loads to an HPLC Bio-Sil TSK-545 DEAE column (150×21.5 mm) (BioRad Laboratories, Hercules, Calif.) equilibrated in PEM at 4° C. After an equilibration period, a 120-ml wash of 50 mM NaCl in PEM was followed by a 120-ml linear gradient (50–200 mM NaCl in PEM) elution at a flow rate of 2 ml/minute. Appropriate fractions were pooled and concentrated in dialysis tubing against Sephadex G-200 (Boehringer Mannheim Biochemicals, UK) to a final volume of 1.5 ml. The concentrated cGB-PDE pool was applied to an HPLC gel filtration column (Bio-Sil TSK-250, 500×21.5 mm) equilibrated in 100 mM sodium phosphate, pH 6.8, 2 mM EDTA, 25 mM β-mercaptoethanol and eluted with a flow rate of 2 ml/minute at 4° C.

If the modified, less cumbersome procedure was performed, the protein pool was dialyzed against PEM for 2 hours and loaded onto a 10 ml preparative DEAE Sephacel column (Pharmacia) equilibrated in PEM buffer. The protein was eluted batchwise with 0.5M NaCl in PEM, resulting in an approximately 10–15 fold concentration of protein. The concentrated protein sample was loaded onto an 800 ml (2.5 cm×154 cm) Sephacryl S400 gel filtration column (Boehringer) equilibrated in 0.1M NaCl in PEM, and eluted at a flow rate of 1.7 ml/minute.

The purity of the protein was assessed by Coomassie staining after sodium dodecyl sulfate-polyacrylamide gel electrophoresis (SDS-PAGE). Approximately 0.5–3.0 mg of pure cGB-PDE were obtained per 10 kg bovine lung.

Rabbit polyclonal antibodies specific for the purified bovine cGB-PDE were generated by standard procedures.

B. Amino Acid Sequencing of cGB-PDE cGB-PDE phosphorylated with [$^{32}$P]ATP and was then digested with protease to yield $^{32}$P-labelled phosphopeptides. Approximately 100 µg of purified cGB-PDE was phosphorylated in a reaction mixture containing 9 mM $MgCl_2$, 9 µM [$^{32}$P]ATP, 10 µM cGMP, and 4.2 µg purified bovine catalytic subunit of cAMP-dependent protein kinase (cAK) in a final volume of 900 µl. Catalytic subunit of cAK was prepared according to the method of Flockhart et al., pp. 209–215 in Marangos et al., Brain Receptor Methodologies, Part A, Academic Press, Orlando, Fla. (1984). The reaction was incubated for 30 minutes at 30° C., and stopped by addition of 60 µl of 200 mM EDTA.

To obtain a first peptide sequence from cGB-PDE, 3.7 µl of a 1 mg/ml solution of a α-chymotrypsin in KPE buffer (10 mM potassium phosphate, pH 6.8, with 2 mM EDTA) was added to 100 µg purified, phosphorylated cGB-PDE and the mixture was incubated for 30 minutes at 30° C. Proteolysis was stopped by addition of 50 µl of 10% SDS and 25 µl of β-mercaptoethanol. The sample was boiled until the volume was reduced to less than 400 µl, and was loaded onto an 8% preparative SDS-polyacrylamide gel and subjected to electrophoresis at 50 mAmps. The separated digestion products were electroblotted onto Immobilon polyvinylidene difluoride (Millipore, Bedford, Mass.), according to the method of Matsudaira, *J. Biol. Chem*, 262:10035–10038 (1987). Transferred protein was identified by Coomassie Blue staining, and a 50 kDa band was excised from the membrane for automated gas-phase amino acid sequencing. The sequence of the peptide obtained by the α-chymotryptic digestion procedure is set out below as SEQ ID NO: 1.

SEQ ID NO: 1 REXDANRINYMYAQYVKNTM

A second sequence was obtained from a cGB-PDE peptide fragment generated by V8 proteolysis. Approximately 200 µg of purified cGB-PDE was added to 10 mM $MgCl_2$, 10 µM [$^{32}$P]ATP, 100 µM cGMP, and 1 µg/ml purified catalytic subunit of cAK in a final volume of 1.4 ml. The reaction was incubated for 30 minutes at 30° C., and was terminated by the addition of 160 µl of 0.2M EDTA. Next, 9 µl of 1 mg/ml *Staphylococcal aureus* V8 protease (International Chemical Nuclear Biomedicals, Costa Mesa, Calif.) diluted in KPE was added, followed by a 15 minute incubation at 30° C. Proteolysis was stopped by addition of 88 µl of 10% SDS and 45 µl β-mercaptoethanol. The digestion products were separated by electrophoresis on a preparative 10% SDS-polyacrylamide gel run at 25 mAmps for 4.5 hours. Proteins were electroblotted and stained as described above. A 28 kDa protein band was excised from the membrane and subjected to automated gas-phase amino acid sequencing. The sequence obtained is set out below as SEQ ID NO: 2.

SEQ ID NO: 2 QSLAAAVVP

C. PCR Amplification of Bovine cDNA

The partial amino acid sequences utilized to design primers (SEQ ID NO: 3, below, and amino acids 9–20 of SEQ ID NO: 1) and the sequences of the corresponding PCR primers (in IUPAC nomenclature) are set below wherein SEQ ID NO: 3 is the sequence reported in Thomas I, supra.

SEQ ID NO: 3

F   D   N   D   E   G   E   Q
5' TTY GAY AAY GAY GAR GGN GAR CA 3' (SEQ ID NO: 4)

3' AAR CTR TTR CTR CTY CCN CTY GT 5' (SEQ ID NO: 5)

SEQ ID NO: 1, Amino acids 9–20

N   Y   M   Y   A   Q   Y   V   K   N   T   M
5' AAY TAY ATG TAY GCN CAR TAY GT 3' (SEQ ID NO: 6)

3' TTR ATR TAC ATR CGN GTY ATR CA 5' (SEQ ID NO: 7)

3' TTR ATR TAC ATR CGN GTY ATR CAN TTY TTR TGN TAC 5' (SEQ ID NO: 8)

The sense and antisense primers, synthesized using an Applied Biosystems Model 380A DNA Synthesizer (Foster City, Calif.), were used in all possible combinations to amplify cGB-PDE-specific sequences from bovine lung first strand cDNA as described below.

After ethanol precipitation, pairs of oligonucleotides were combined (SEQ ID NO: 4 or 5 combined with SEQ ID NOs: 6, 7 or 8) at 400 nM each in a PCR reaction. The reaction was run using 50 ng first strand bovine lung cDNA (generated using AMV reverse transcriptase and random primers on oligo dT selected bovine lung mRNA), 200 µM dNTPs, and 2 units of Taq polymerase. The initial denaturation step was carried out at 94° C. for 5 minutes, followed by 30 cycles of a 1 minute denaturation step at 94° C., a two minute annealing step at 50° C., and a 2 minute extension step at 72° C. PCR was performed using a Hybaid Thermal Reactor (ENK Scientific Products, Saratoga, Calif.) and products were separated by gel electrophoresis on a 1% low melting point agarose gel run in 40 mM Tris-acetate, 2 mM EDTA. A weak band of about 800–840 bp was seen with the primers set out in SEQ ID NOs: 4 and 7 and with primers set out in SEQ ID NOs: 4 and 8. None of the other primer pairs yielded visible bands. The PCR product generated by amplification with the primers set out in SEQ ID NOs: 4 and 7 was isolated using the Gene Clean® (Bio101, La Jolla, Calif.) DNA purification kit according to the manufacturer's protocol. The PCR product (20 ng) was ligated into 200 ng of linearized pBluescript KS(+) (Stratagene, La Jolla, Calif.), and the resulting plasmid construct was used to transform *E. coli* XL1 Blue cells (Stratagene Cloning Systems, La Jolla, Calif.). Putative transformation positives were screened by sequencing. The sequences obtained were not homologous to any known PDE sequence or to the known partial cGB-PDE sequences.

PCR was performed again on bovine lung first strand cDNA using the primers set out in SEQ ID NOs: 4 and 7. A clone containing a 0.8 Kb insert with a single large open reading frame was identified. The open reading frame encoded a polypeptide that included the amino acids KNTM (amino acids 17–20 of SEQ ID NO: 1 which were not utilized to design the primer sequence which is set out in SEQ ID NO: 7) and that possessed a high degree of homology to the deduced amino acid sequences of the cGs-, ROS- and COS-PDEs. The clone identified corresponds to nucleotides 489–1312 of SEQ ID NO: 9.

D. Construction and Hybridization Screening of a Bovine cDNA Library

In order to obtain a cDNA encoding a full-length cGB-PDE, a bovine lung cDNA library was screened using the $^{32}$P-labelled PCR-generated cDNA insert as a probe.

Polyadenylated RNA was prepared from bovine lung as described Sonnenburg et al., *J. Biol. Chem.*, 266:17655–17661 (1991). First strand cDNA was synthesized using AMV reverse transcriptase (Life Sciences, St. Petersburg, Fla.) with random hexanucleotide primers as described in Ausubel et al., *Current Protocols in Molecular Biology*, John Wiley & Sons, New York (1987). Second strand cDNA was synthesized using *E. coli* DNA polymerase I in the presence of *E. coli* DNA ligase and *E. coli* RNAse H. Selection of cDNAs larger than 5130 bp was performed by Sepharose® CL-4B (Millipore) chromatography. EcoRI adaptors (Promega, Madison, Wis.) were ligated to the cDNA using T4 DNA ligase. Following heat inactivation of the ligase, the cDNA was phosphorylated using T4 polynucleotide kinase. Unligated adaptors were removed by Sepharose® CL-4B chromatography (Pharmacia, Piscataway, N.J.). The cDNA was ligated into EcoRI-digested, dephosphorylated lambda Zap®II arms (Stratagene) and packaged with Gigapack® Gold (Stratagene) extracts according to the manufacturer's protocol. The liter of the unamplified library was $9.9\times10^5$ with 18% nonrecombinants. The library was amplified by plating 50,000 plaque forming units (pfu) on to twenty 150 mm plates, resulting in a final titer of $5.95\times10^6$ pfu/ml with 21% nonrecombinants.

The library was plated on twenty-four 150 mm plates at 50,000 pfu/plate, and screened with the $^{32}$P-labelled cDNA clone. The probe was prepared using the method of Feinberg et al., *Anal Biochem.*, 137:266–267 (1984), and the $^{32}$P-labelled DNA was purified using Elutip-D® columns (Schleicher and Schuell Inc., Keene, N.H.) using the manufacturer's protocol. Plaque-lifts were performed using 15 cm nitrocellulose filters. Following denaturation and neutralization, DNA was fixed onto the filters by baking at 80° C. for 2 hours. Hybridization was carried out at 42° C. overnight in a solution containing 50% formamide, 5× SSC (0.75M NaCl, 0.75M sodium titrate, pH 7), 25 mM sodium phosphate (pH 7.0), 2×Denhardt's solution, 10% dextran sulfate, 90 µg/ml yeast tRNA, and approximately $10^6$ cpm/ml $^{32}$P-labelled probe ($5\times10^8$ cpm/µg). The filters were washed twice in 0.1× SSC, 0.1% SDS at room temperature for 15 minutes per wash, followed by a single 20 minute wash in 0.1× SSC, 1% SDS at 45° C. The filters were then exposed to X-ray film at −70° C. for several days.

Plaques that hybridized with the labelled probe were purified by several rounds of replating and rescreening. Insert cDNAs were subcloned into the pBluescript SK(−) vector (Stratagene) by the in vivo excision method described by the manufacturer's protocol. Southern blots were performed in order to verify that the rescued cDNA hybridized to the PCR probe. Putative cGB-PDE cDNAs were sequenced using Sequenase® Version 2.0 (United States Biochemical Corporation, Cleveland, Ohio) or TaqTrack® kits (Promega).

Three distinct cDNA clones designated cGB-2, cGB-8 and cGB-10 were isolated. The DNA and deduced amino acid sequences of clone cGB-8 are set out in SEQ ID NOs: 9 and 10. The DNA sequence downstream of nucleotide 2686 may represent a cloning artifact. The DNA sequence of cGB-10 is identical to the sequence of cGB-8 with the exception of one nucleotide. The DNA sequence of clone cGB-2 diverges from that of clone cGB-8 5' to nucleotide 219 of clone cgb-8 (see SEQ ID NO: 9) and could encode a protein with a different amino terminus.

The cGB-8 cDNA clone is 4474 bp in length and contains a large open reading frame of 2625 bp. The triplet ATG at position 99–101 in the nucleotide sequence is predicted to be the translation initiation site of the cGB-PDE gene because it is preceded by an in-frame stop codon and the surrounding bases are compatible with the Kozak consensus initiation site for eucaryotic mRNAs. The stop codon TAG is located at positions 2724–2726, and is followed by 1748 bp of 3' untranslated sequence. The sequence of cGB-8 does not contain a transcription termination consensus sequence, therefore the clone may not represent the entire 3' untranslated region of the corresponding mRNA.

The open reading frame of the cGB-8 cDNA encodes an 875 amino acid polypeptide with a calculated molecular mass of 99.5 kD. This calculated molecular mass is only slightly larger than the reported molecular mass of purified cGB-PDE, estimated by SDS-PAGE analysis to be approximately 93 kDa. The deduced amino acid sequence of cGB-8 corresponded exactly to all peptide sequences obtained from purified bovine lung cGB-PDE providing strong evidence that cGB-8 encodes cGB-PDE.

EXAMPLE 2

A search of the SWISS-PROT and GEnEmbl data banks (Release of February, 1992) conducted using the FASTA program supplied with the Genetics Computer Group (GCG) Software Package (Madison, Wis.) revealed that only DNA and amino acid sequences reported for other PDEs displayed significant similarity to the DNA and deduced amino acid of clone cGB-8.

Pairwise comparisons of the cGB-PDE deduced amino acid sequence with the sequences of eight other PDEs were conducted using the ALIGN [Dayhoff et al, *Methods*

Enzymol., 92:524-545 (1983)] and BESTFIT [Wilbur et al., Proc. Natl. Acad. Sci. U.S.A., 80:726-730 (1983)] programs. Like all mammalian phosphodiesterases sequenced to date, cGB-PDE contains a conserved catalytic domain sequence of approximately 250 amino acids in the carboxyl-terminal half of the protein that is thought to be essential for catalytic activity. This segment comprises amino acids 578-812 of SEQ ID NO: 9 and exhibits sequence conservation with the corresponding regions of other PDEs. Table 1 below sets out the specific identity values obtained in pairwise comparisons of other PDEs with amino acids 578-812 of cGB-PDE, wherein "ratdunce" is the rat cAMP-specific PDE; "61 kCaM" is the bovine 61 kDa calcium/calmodulin-dependent PDE; "63 kCaM" is the bovine 63 kDa calcium/calmodulin-dependent PDE; "drosdunce" is the drosophila cAMP-specific dunce PDE; "ROS-α" is the bovine ROS-PDE α-subunit; "ROS-β" is the bovine ROS-PDE β-subunit; "COS-α'" is the bovine COS-PDE α' subunit; and "cGs" is the bovine cGs-PDE (612-844).

TABLE 1

| Phosphodiesterase | Catalytic Domain Residues | % Identity |
|---|---|---|
| Ratdunce | 77-316 | 31 |
| 61 kCaM | 193-422 | 29 |
| 63 kcam | 195-424 | 29 |
| drosdunce | 1-239 | 28 |
| ROS-α | 535-778 | 45 |
| ROS-β | 533-776 | 46 |
| COS-α' | 533-776 | 48 |
| cGs | 612-844 | 40 |

Multiple sequence alignments were performed using the Progressive Alignment Algorithm [Feng et al., Methods Enzymol, 183:375-387 (1990)] implemented in the PILEUP program (GCG Software). FIGS. 1A to 1C shows a multiple sequence alignment of the proposed catalytic domain of cGB-PDE with the all the corresponding regions of the PDEs of Table 1. Twenty-eight residues (see residues indicated by one letter amino acid abbreviations in the "conserved" line on FIGS. 1A to 1C) are invariant among the isoenzymes including several conserved histidine residues predicted to play a functional role in catalysis. See Charbonneau et al., Proc. Natl. Acad. Sci. U.S.A., supra. The catalytic domain of cGB-PDE more closely resembles the catalytic domains of the ROS-PDEs and COS-PDEs than the corresponding regions of other PDE isoenzymes. There are several conserved regions among the photoreceptor PDEs and cGB-PDE that are not shared by other PDEs. Amino acid positions in these regions that are invariant in the photoreceptor PDE and cGB-PDE sequences are indicated by stars in the "conserved" line of FIGS. 1A to 1C. Regions of homology among cGB-PDE and the ROS- and COS-PDEs may serve important roles in conferring specificity for cGMP hydrolysis relative to cAMP hydrolysis or for sensitivity to specific pharmacological agents.

Sequence similarity between cGB-PDE, cGs-PDE and the photoreceptor PDEs, is not limited to the conserved catalytic domain but also includes the noncatalytic cGMP binding domain in the amino-terminal half of the protein. Optimization of the alignment between cGB-PDE, cGs-PDE and the photoreceptor PDEs indicates that an amino-terminal conserved segment may exist including amino acids 142-526 of SEQ ID NO: 9. Pairwise analysis of the sequence of the proposed cGMP-binding domain of cGB-PDE with the corresponding regions of the photoreceptor PDEs and cGs-PDE revealed 26-28% sequence identity. Multiple sequence alignment of the proposed cGMP-binding domains with the cGMP-binding PDEs is shown in FIGS. 2A to 2C wherein abbreviations are the same as indicated for Table 1. Thirty-eight positions in this noncatalytic domain appear to be invariant among all cGMP-binding PDEs (see positions indicated by one letter amino acid abbreviations in the "conserved" line of FIGS. 2A to 2C).

The cGMP-binding domain of the cGMP-binding PDEs contains internally homologous repeats which may form two similar but distinct inter- or intra-subunit cGMP-binding sites. FIG. 3 shows a multiple sequence alignment of the repeats a (corresponding to amino acids 228-311 of cGB-PDE) and b (corresponding to amino acids 410-500 of cGB-PDE) of the cGMP-binding PDEs. Seven residues are invariant in each A and B regions (see residues indicated by one letter amino acid abbreviations in the "conserved" line of FIG. 3). Residues that are chemically conserved in the A and B regions are indicated by stars in the "conserved" line of FIG. 3. cGMP analog studies of cGB-PDE support the existence of a hydrogen bond between the cyclic nucleotide binding site on cGB-PDE and the 2'OH of cGMP.

Three regions of cGB-PDE have no significant sequence similarity to other PDE isoenzymes. These regions include the sequence flanking the carboxyl-terminal end of the catalytic domain (amino acids 812-875), the sequence separating the cGMP-binding and catalytic domains (amino acids 527-577) and the amino-terminal sequence spanning amino acids 1-141. The site (the serine at position 92 of SEQ ID NO: 10) of phosphorylation of cGB-PDE by cGK is located in this amino-terminal region of sequence. Binding of cGMP to the allosteric site on cGB-PDE is required for its phosphorylation.

A proposed domain structure of cGB-PDE based on the foregoing comparisons with other PDE isoenzymes is presented in FIG. 4. This domain structure is supported by the biochemical studies of cGB-PDE purified from bovine lung.

EXAMPLE 3

The presence of cGB-PDE mRNA in various bovine tissues was examined by Northern blot hybridization.

Polyadenylated RNA was purified from total RNA preparations using the Poly(A) Quick® mRNA purification kit (Stratagene) according to the manufacturer's protocol. RNA samples (5 μg) were loaded onto a 1.2% algarose, 6.7% formaldehyde gel. Electrophoresis and RNA transfer were performed as previously described in Sonnenburg et al., supra. Prehybridization of the RNA blot was carried out for 4 hours at 45° C. in a solution containing 50% formamide, 5× SSC, 25 mM sodium phosphate, pH 7, 2× Denhardt's solution, 10% dextran sulfate, and 0.1 mg/ml yeast tRNA. A random hexanueleotide-primer-labelled probe ($5 \times 10^8$ cpm/μg) was prepared as described in Feinberg et al., supra, using the 4.7 kb eGB-8 cDNA clone of Example 2 excised by digestion with AccI and SacII. The probe was heat denatured and injected into a blotting bag ($6 \times 10^8$ cpm/ml) following prehybridization. The Northern blot was hybridized overnight at 45° C., followed by one 15 minute wash with 2× SSC, 0.1% SDS at room temperature, and three 20 minute washes with 0.1× SSC, 0.1% SDS at 45° C. The blot was exposed to X-ray film for 24 hours at −70° C. The size of the RNA that hybridized with the cGB-PDE probe was estimated using a 0.24-9.5 kb RNA ladder that was stained with ethidium bromide and visualized with UV light.

The $^{32}$P-labelled cGB-PDE cDNA hybridized to a single 6.8 kb bovine lung RNA species. A mRNA band of the identical size was also detected in polyadenylated RNA isolated from bovine trachea, aorta, kidney and spleen.

EXAMPLE 4

The cGB-PDE cDNA in clone cGB-8 of Example 2 was expressed in COS-7 cells (ATCC CRL1651).

A portion of the cGB-8 cDNA was isolated following digestion with the restriction enzyme XbaI. XbaI cut at a position in the pBluescript polylinker sequence located 30 bp upstream of the 5' end of the cGB-8 insert and at position 3359 within the cGB-8 insert. The resulting 3389 bp fragment, which contains the entire coding region of cGB-8, was then ligated into the unique XbaI cloning site of the expression vector pCDM8 (Invitrogen, San Diego, Calif.). The pCDM8 plasmid is a 4.5 kb eucaryotic expression vector containing a cytomegalovirus promoter and enhancer, an SV40-derived origin of replication, a polyadenylation signal, a procaryotic origin of replication (derived from pBR322) and a procaryotic genetic marker (supF). *E. coli* MC1061/P3 cells (Invitrogen) were transformed with the resulting ligation products, and transformation positive colonies were screened for proper orientation of the cGB-8 insert using PCR and restriction enzyme analysis. The resulting expression construct containing the cGB-8 insert in the proper orientation is referred to as pCDMS-cGB-PDE.

The pCDM8-cGB-PDE DNA was purified from large-scale plasmid preparations using Qiagen pack-500 columns (Chatsworth, Calif.) according to the manufacturer's protocol. COS-7 cells were cultured in Dulbecco's modified Eagle's medium (DMEM) containing 10% fetal bovine serum, 50 µg/ml penicillin and 50 µg/ml streptomycin at 37° C. in a humidified 5% $CO_2$ atmosphere. Approximately 24 hours prior to transfection, confluent 100 mm dishes of cells were replated at one-fourth or one-fifth the original density. In a typical transfection experiment, cells were washed with buffer containing 137 mM NaCl, 2.7 mM KCl, 1.1 mM potassium phosphate, and 8.1 mM sodium phosphate, pH 7.2 (PBS). Then 4–5 ml of DMEM containing 10% NuSerum (Collaborative Biomedical Products, Bedford, Mass.) was added to each plate. Transfection with 10 µg pCDM8-cGB-PDE DNA or pCDM8 vector DNA mixed with 400 µg DEAE-dextran (Pharmacia) in 60 µl TBS [Tris-buffered saline: 25 mM Tris-HCl (pH 7.4), 137 mM NaCl, 5 mM KCl, 0.6 mM $Na_2HPO_4$, 0.7 mM $CaCl_2$, and 0.5 mM $MgCl_2$] was carried out by dropwise addition of the mixture to each plate. The cells were incubated at 37° C., 5% $CO_2$ for 4 hours, and then treated with 10% dimethyl sulfoxide in PBS for 1 minute. After 2 minutes, the dimethyl sulfoxide was removed, the cells were washed with PBS and incubated in complete medium. After 48 hours, cells were suspended in 0.5–1 ml of cold homogenization buffer [40 mM Tris-HCl (pH 7.5), 15 mM benzamidine, 15 mM β-mercaptoethanol, 0.7 µg/ml pepstalin A, 0.5 µg/ml leupeptin, and 5 µM EDTA] per plate of cells, and disrupted using a Dounce homogenizer. The resulting whole-cell extracts were assayed for phosphodiesterase activity, cGMP-binding activity, and total protein concentration as described below in Example 5.

EXAMPLE 5

Phosphodiesterase activity in extracts of the transfected COS cells of Example 4 or in extracts of mock transfected COS cells was measured using a modification of the assay procedure described for the cGs-PDE in Martins et al., *J. Biol. Chem.*, 257:1973–1979 (1982). Cells were harvested and extracts prepared 48 hours after transfection. Incubation mixtures contained 40 mM MOPS buffer (pH 7), 0.8 mM EDTA, 15 mM magnesium acetate, 2 mg/ml bovine serum albumin, 20 µM [$^3$H]cGMP or [$^3$H]cAMP (100,000–200,000 cpm/assay) and COS-7 cell extract in a total volume of 250 µl. The reaction mixture was incubated for 10 minutes at 30° C., and then stopped by boiling. Next, 10 µl of 10 mg/ml *Crotalus atrox* venom (Sigma) was added followed by a 10 minute incubation at 30° C. Nucleoside products were separated from unreacted nucleotides as described in Martins et al., supra. In all studies, less than 15% of the total [$^3$H]cyclic nucleotide was hydrolyzed during the reaction.

Figure 5:
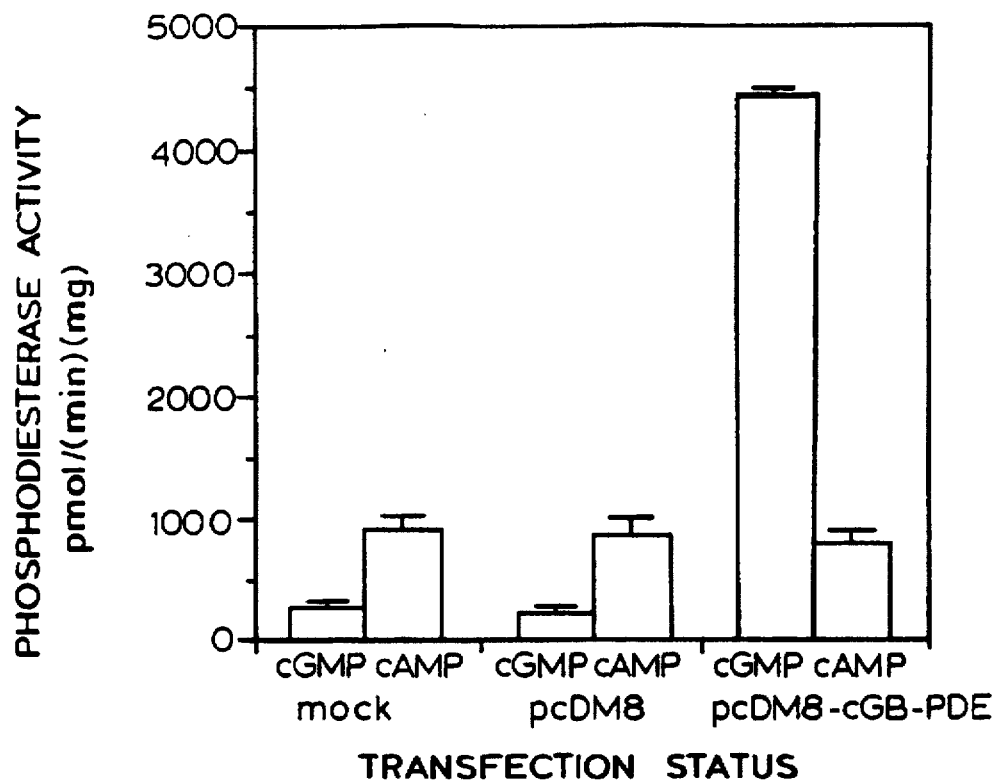
FIG. 5 is a bar graph representing the results of experiments in which extracts of COS cells transfected with bovine cGB-PDE sequences or extracts of untransfected COS cells were assayed for phosphodiesterase activity using either 20 µM cGMP or 20 µM cAMP as the substrate.

The results of the assays are presented in FIG. 5 wherein the results shown are averages of three separate transfections. Transfection of COS-7 cells with pCDMS-cGB-PDE DNA resulted in the expression of approximately 15-fold higher levels of cGMP phosphodiesterase activity than in mock-transfected cells or in cells transfected with pCDM8 vector alone. No increase in cAMP phosphodiesterase activity over mock or vector-only transfected cells was detected in extracts from cells transfected with pCDMS-cGB-PDE DNA. These results confirm that the cGB-PDE bovine cDNA encodes a cGMP-specific phosphodiesterase.

Extracts from the transfected COS cells of Example 4 were also assayed for cGMP PDE activity in the presence of a series of concentrations of the PDE inhibitors zaprinast, dipyridamole (Sigma), isobutyl-1-methyl-8-methoxymethylxanthine (MeOxMeMIX) and rolipram.

Figure 6:
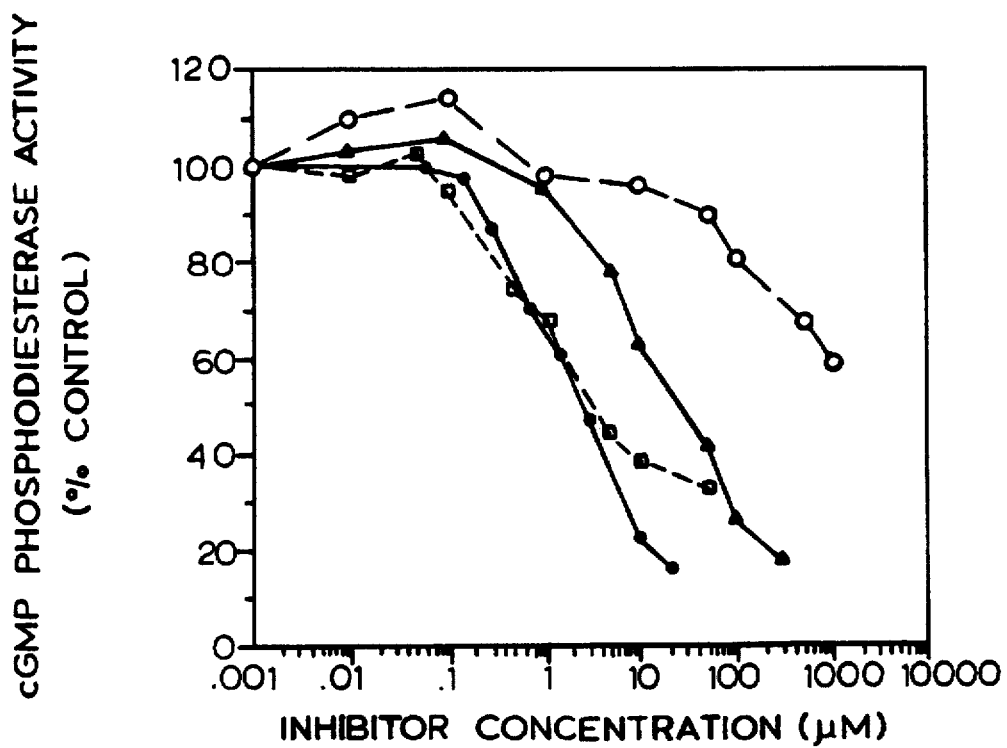
FIG. 6 is a graph depicting results of assays of extracts from cells transfected with bovine cGB-PDE sequences for cGMP phosphodiesterase activity in the presence of a series of concentrations of phosphodiesterase inhibitors including dypyridamole (closed squares), zaprinast (closed circles), methoxymethylxanthine (closed triangles) and rolipram (open circles)

The results of the assays are presented in FIG. 6 wherein PDE activity in the absence of inhibitor is taken as 100% and each data point represents the average of two separate determinations. The relative potencies of PDE inhibitors for inhibition of cGMP hydrolysis by the expressed cGB-BPDE cDNA protein product were identical to those relative potencies reported for native cGB-PDE purified from bovine lung (Thomas I, supra). $IC_{50}$ values calculated from the curves in FIG. 6 are as follows: zaprinast (closed circles), 2 µM; dipyridamole (closed squares), 3.5 µM; MeOxMeMIX (closed triangles), 30 µM; and rolipram (open circles), >300 µM. The $IC_{50}$ value of zaprinast, a relatively specific inhibitor of cGMP-specific phosphodiesterases, was at least two orders of magnitude lower than that reported for inhibition of phosphodiesterase activity of the cGs-PDE or of the cGMP-inhibited phosphodiesterase (cGi-PDEs) (Reeves et al., pp. 300–316 in Beavo et al., supra). Dipyrimadole, an effective inhibitor of selected cAMP- and cGMP-specific phosphodiesterases, was also a potent inhibitor of the expressed cGB-PDE. The relatively selective inhibitor of calcium/calmodulin-stimulated phosphodiesterase (CaM-PDEs), MeOxMeMIX, was approximately 10-fold less potent than zaprinast and dipyridamole, in agreement with results using cGB-PDE activity purified from bovine lung. Rolipram, a potent inhibitor of low $K_m$ cAMP phosphodisterases, was a poor inhibitor of expressed cGB-PDE cDNA protein product. These results show that the cGB-PDE cDNA encodes a phosphodiesterase that possesses catalytic activity characteristic of cGB-PDE isolated from bovine tissue, thus verifying the identity of the cGB-8 cDNA clone as a cGB-PDE.

It is of interest to note that although the relative potencies of the PDE inhibitors for inhibition of cGMP hydrolysis were identical for the recombinant and bovine isolate cGB-PDE, the absolute $IC_{50}$ values for all inhibitors tested were 2–7 fold higher for the recombinant cGB-PDE. This difference could not be attributed to the effects of any factors present in COS-7 cell extracts on cGMP hydrolytic activity, since cGB-PDE isolated from bovine tissue exhibited identical kinetics of inhibition as a pure enzyme, or when added back to extracts of mock-transfected COS-7 cells. This apparent difference in pharmacological sensitivity may be due to a subtle difference in the structure of the recombinant cGB-PDE cDNA protein product and bovine lung cGB- PDE, such as a difference in post-translational modification at or near the catalytic site. Alternatively, this difference may be due to an alteration of the catalytic activity of bovine lung cGB-PDE over several purification steps.

Cell extracts were assayed for [$^3$H]cGMP-binding activity in the absence or presence of 0.2 mM 3-isobutyl-1-methylxanthine (IBMX) (Sigma), a competitive inhibitor of cGMP hydrolysis. The cGMP binding assay, modified from the assay described in Thomas I, supra, was conducted in a total volume of 80 μl. Sixty μl of cell extract was combined with 20 μl of a binding cocktail such that the final concentration of components of the mixture were 1 μM [$^3$H]cGMP, 5 μM cAMP, and 10 μM 8-bromo-cGMP. The cAMP and 8-bromo-cGMP were added to block [$^3$H]cGMP binding to cAK and cGK, respectively. Assays were carried out in the absence and presence of 0.2 mM IBMX. The reaction was initiated by the addition of the cell extract, and was incubated for 60 minutes at 0° C. Filtration of the reaction mixtures was carried out as described in Thomas I, supra. Blanks were determined by parallel incubations with homogenization buffer replacing cell extracts, or with a 100-fold excess of unlabelled cGMP. Similar results were obtained with both methods. Total protein concentration of the cell extracts was determined by the method of Bradford, *Anal Biochem.*, 72:248–254 (1976) using bovine serum albumin as the standard.

Figure 7:
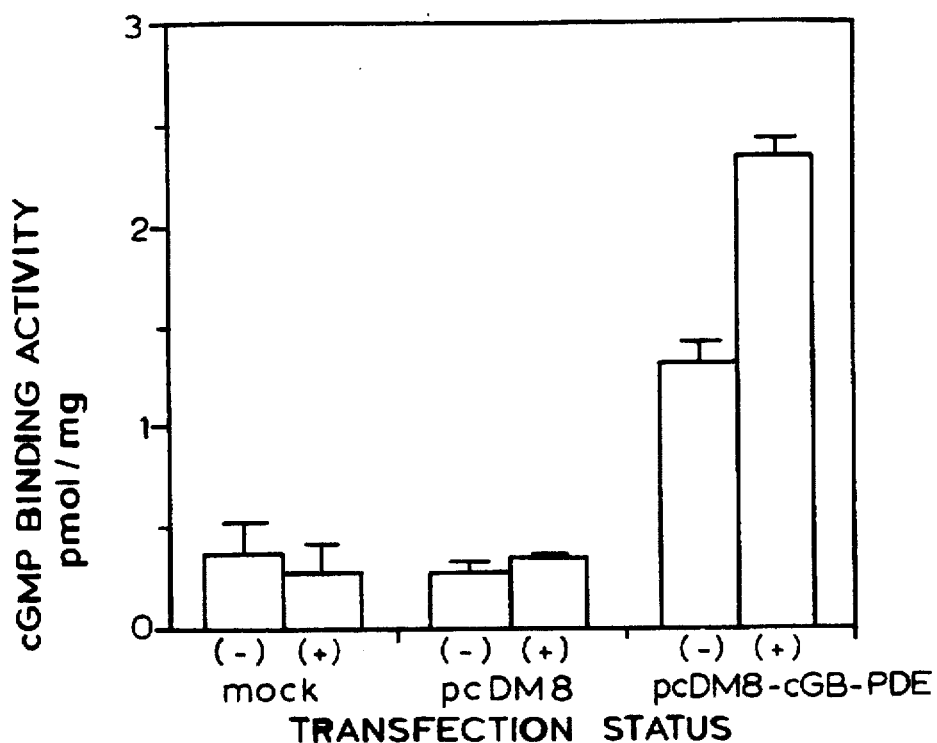
FIG. 7 is a bar graph presenting results of experiments in which cell extracts from COS cells transfected with bovine cGB-PDE sequences or control untransfected COS cells were assayed for [$^3$H]cGMP-binding activity in the absence (−) or presence (+) of 0.2 mM IBMX.

Results of the assay are set out in FIG. 7. When measured at 1 μM [$^3$H]cGMP in the presence of 0.2 mM IBMX, extracts from COS-7 cells transfected with pCDMS-cGB-PDE exhibited 8-fold higher cGMP-binding activity than extracts from mock-transfected cells. No IBMX stimulation of background cGMP binding was observed suggesting that little or no endogenous cGB-PDE was present in the COS-7 cell extracts. In extracts of pCDMS-cGB-PDE transfected cells cGMP-specific activity was stimulated approximately 1.8-fold by the addition of 0.2 mM IBMX. The ability of IBMX to stimulate cGMP binding 2–5 fold is a distinctive property of the cGMP-binding phosphodiesterases.

Figure 8:
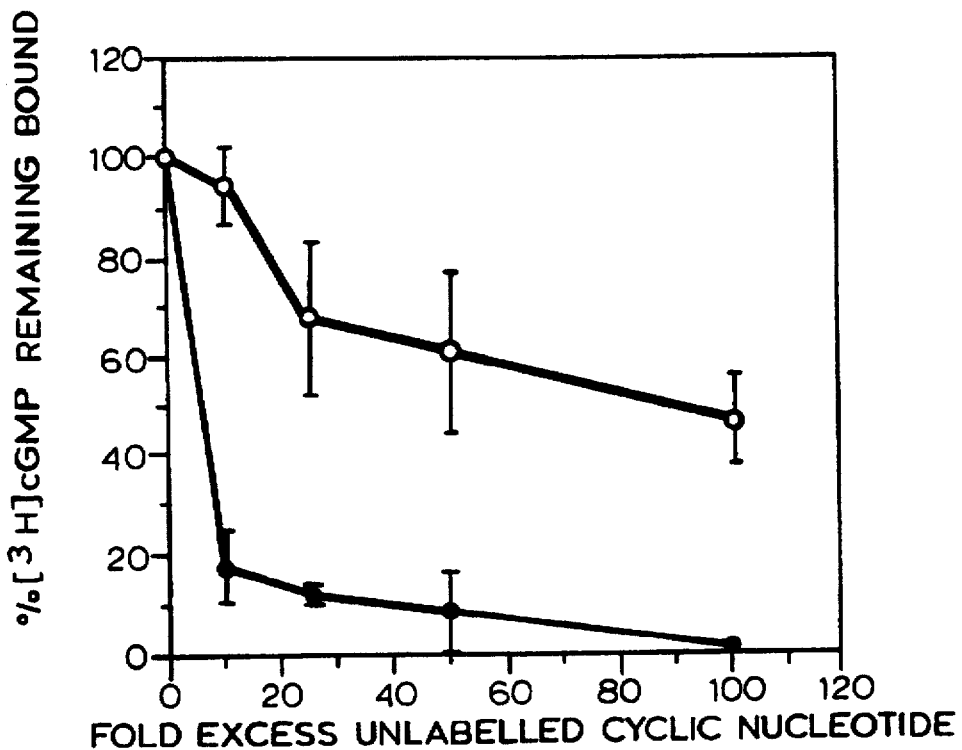
FIG. 8 is a graph of the results of assays in which extracts from cells transfected with bovine cGB-PDE sequences were assayed for [$^3$H]cGMP-binding activity in the presence of excess unlabelled cAMP (open circles) or cGMP (closed circles) at the concentrations indicated.

Cell extracts were assayed as described above for [$^3$H] cGMP-binding activity (wherein concentration of [$^3$H] cGMP was 2.5 μM) in the presence of excess unlabelled cAMP or cGMP. Results are presented in FIG. 8 wherein cGMP binding in the absence of unlabelled competitor was taken as 100% and each data point represents the average of three separate determinations. The binding activity of the protein product encoded by the cGB-PDE cDNA was specific for cGMP relative to cAMP. Less than 10-fold higher concentrations of unlabelled cGMP were required to inhibit [$^3$H]cGMP binding activity by 50% whereas approximately 100-fold higher concentrations of cAMP were required for the same degree of inhibition.

The results presented in this example show that the cGB-PDE cDNA encodes a phosphodiesterase which possesses biochemical activities characteristic of native cGB-PDE.

The catalytic domains of mammalian PDEs and a Drosophila PDE contain two tandem conserved sequences (HX$_3$HX$_{24}$-$_{26}$E) that are typical Zn$^{2+}$-binding motifs in Zn$^{2+}$ hydrolases such as thermolysin [Vallee and Auld, *Biochem.*, 29: 5647–5659 (1990)]. cGB-PDE binds Zn$^{2+}$ in the presence of large excesses of Mg$^{2+}$, Mn$^{2+}$, Fe$^{2+}$, Fe$^{3+}$, Ca$^{2+}$ or Cd$^{2+}$. In the absence of added metal, cGB-PDE has a PDE activity that is approximately 20% of the maximum activity that occurs in the presence of 40 mM Mg$^{2+}$, and this basal activity is inhibited by 1,10-phenanthroline or EDTA. This suggests that a trace metal(s) accounts for the basal PDE activity despite exhaustive treatments to remove metals. PDE activity is stimulated by addition of Zn$^{2+}$ (0.02–1 μM) or Co$^{2+}$ (1–20 μM), but not by Fe$^{2+}$, Fe$^{3+}$, Cot$^{2+}$, Cd$^{2+}$, or Cu$^{2+}$. Zn$^{2+}$ increases the basal PDE activity up to 70% of the maximum stimulation produced by 40 mM Mg$^{2+}$. The stimulatory effect of Zn$^{2+}$ in these assays may be compromised by an inhibitory effect that is caused by Zn$^{2+}$ concentrations >1 μM. The Zn$^{2+}$-supported PDE activity and Zn$^{2+}$ binding by cGB-PDE occur at similar concentrations of Zn$^{2+}$. cGB-PDE thus appears to be a Zn$^{2+}$ hydrolase and Zn$^{2+}$ appears to play a critical role in the activity of the enzyme. See, Colbran et al., *The FASEB J.*, 8: Abstract 2148 (Mar. 15, 1994).

EXAMPLE 6

Several human cDNA clones, homologous to the bovine cDNA clone encoding cGB-PDE, were isolated by hybridization under stringent conditions using a nucleic acid probe corresponding to a portion of the bovine cGB-8 clone (nucleotides 489–1312 of SEQ ID NO: 9).

Isolation of cDNA Fragments Encoding Human cGB-PDE

Three human cDNA libraries (two glioblastoma and one lung) in the vector lambda Zap were probed with the bovine cGB-PDE sequence. The PCR-generated clone corresponding to nucleotides 484–1312 of SEQ ID NO: 9 which is described in Example 1 was digested with EcoRI and SalI and the resulting 0.8 kb cDNA insert was isolated and purified by agarose gel electrophoresis. The fragment was labelled with radioactive nucleotides using a random primed DNA labelling kit (Boehringer).

The cDNA libraries were plated on 150 mm petri plates at a density of approximately 50,000 plaques per plate. Duplicate nitrocellulose filter replicas were prepared. The prehybridization buffer was 3× SSC, 0.1% sarkosyl, 10× Denhardt's, 20 mM sodium phosphate (pH 6.8) and 50 μg/ml salmon testes DNA. Prehybridization was carried out at 65° C. for a minimum of 30 minutes. Hybridization was carried out at 65° C. overnight in buffer of the same composition with the addition of 1–5×10$^5$ cpm/ml of probe. The filters were washed at 65° C. in 2× SSC, 0.1% SDS. Hybridizing plaques were detected by autoradiography. The number of cDNAs that hybridized to the bovine probe and the number of cDNAs screened are indicated in Table 2 below.

TABLE 2

| cDNA Library | Type | Positive Plaques | Plaques Screened |
|---|---|---|---|
| Human SW 1088 glioblastoma | dT-primed | 1 | 1.5 × 10$^6$ |
| Human lung | dT-primed | 2 | 1.5 × 10$^6$ |
| Human SW 1088 glioblastoma | dT-primed | 4 | 1.5 × 10$^6$ |

Plasmids designated cgbS2.1, cgbS3.1, cgbL23.1, cgbL27.1 and cgbS27.1 were excised in vivo from the lambda Zap clones and sequenced.

Clone cgbS3.1 contains 2060 bp of a PDE open reading frame followed by a putative intron. Analysis of clone cgbS2.1 reveals that it corresponds to done cgbS3.1 positions 664 to 2060 and extends the PDE open reading frame an additional 585 bp before reading into a putative intron. The sequences of the putative 5' untranslated region and the protein encoding portions of the cgbS2.1 and cgbS3.1 clones are set out in SEQ ID NOs: 11 and 12, respectively. Combining the two cDNAs yields a sequence containing approximately 2.7 kb of an open reading encoding a PDE.

The three other cDNAs did not extend any further 5' or 3' than cDNA cgbS3.1 or cDNA cgbS2.1.

To isolate additional cDNAs, probes specific for the 5' end of clone cgbS3.1 and the 3' end of clone cgbS2.1 were prepared and used to screen a SW1088 glioblastoma cDNA library and a human aorta cDNA library. A 5' probe was derived from clone cgbS3.1 by PCR using the primers cgbS3.15311 and cgbL23.1A1286 whose sequences are set out in SEQ ID NOs: 8 and 9, respectively, and below.

Primer cgbS3.15311 (SEQ ID NO: 13) 5' GCCACCA-GAGAAATGGTC 3'

Primer cgbL23.1A1286 (SEQ ID NO: 14) 5' ACAATGGGTCTAAGAGGC 3'

The PCR reaction was carried out in a 50 ul reaction volume containing 50 pg cgbS3.1 cDNA, 0.2 mM dNTP, 10 ug/ml each primer, 50 mM KCl, 10 mM Tris-HCl pH 8.2, 1.5 mM MgCl$_2$ and Taq polymerase. After an initial four minute denaturation at 94° C., 30 cycles of one minute at 94° C., two minutes at 50° C. and four minutes at 72° C. were carried out. An approximately 0.2 kb fragment was generated by the PCR reaction which corresponded to nucleotides 300–496 of clone cgbS3.1.

A 3' probe was derived from cDNA cgbS2.1 by PCR using the oligos cgbL23.1S1190 and cgbS2.1A231 whose sequences are set out below.

Primer cgbL23.1S1190 (SEQ ID NO: 15) 5' TCAGTG-CATGTTTGCTGC 3'

Primer cgbS2.1A231 (SEQ ID NO: 16) 5' TACAAACAT-GTTCATCAG 3'

The PCR reaction as carried out similarly to that described above for generating the 5' probe, and yielded a fragment of approximately 0.8 kb corresponding to nucleotides 1358–2139 of cDNA cgbS2.1. The 3' 157 nucleotides of the PCR fragment (not shown in SEQ ID NO: 12) are within the presumptive intron.

The two PCR fragments were purified and isolated by agarose gel electrophoresis, and were labelled with radioactive nucleotides by random priming. A random-primed SW1088 glioblastoma cDNA library (1.5×10$^6$ plaques) was screened with the labelled fragments as described above, and 19 hybridizing plaques were isolated. An additional 50 hybridizing plaques were isolated from a human aorta cDNA library (dT and random primed, Clontech, Palo Alto, Calif.).

Plasmids were excised in vivo from some of the positive lambda Zap clones and sequenced. A clone designated cgbS53.2, the sequence of which is set out in SEQ ID NO: 17, contains an approximately 1.1 kb insert whose sequence overlaps the last 61 bp of cgbS3.1 and extends the open reading frame an additional 135 bp beyond that found in cgbS2.1. The clone contains a termination codon and approximately 0.3 kB of putative 3' untranslated sequence.

Generation of a Composite cDNA Encoding Human cGB-PDE

Clones cgbS3.1, cgbS2.1 and cgbS53.2 were used as described in the following paragraphs to build a composite cDNA that contained a complete human cGB-PDE opening reading frame. The composite cDNA is designated cgbmet156-2 and was inserted in the yeast ADH1 expression vector pBNY6N.

First, a plasmid designated cgb stop-2 was generated that contained the 3' end of the cGB-PDE open reading frame. A portion of the insert of the plasmid was generated by PCR using clone cgbS53.2 as a template. The PCR primers utilized were cgbS2.1S 1700 and cgbstop-2.

Primer cgbS2.1S1700 (SEQ ID NO: 18) 5' TTTGGAA-GATCCTCATCA 3'

Primer cgbstop-2 (SEQ ID NO: 19) 5' ATGTCTCGAGT-CAGTrCCGCTrGGCCTG 3'

The PCR reaction was carried out in 50 ul containing 50 pg template DNA, 0.2 mM dNTPs, 20 mM Tris-HCl pH 8.2, 10 mM KCl, 6 mM (NH$_4$)$_2$SO$_4$, 1.5 mM MgCl$_2$, 0.1% Triton-X-100, 500 ng each primer and 0.5 units of Pfu polymerase (Stratagene). The reaction was heated to 94° C. for 4 minutes and then 30 cycles of 1 minute at 94° C., 2 minutes at 50° C. and four minutes at 72° C. were performed. The polymerase was added during the first cycle at 50° C. The resulting PCR product was phenol/chloroform extracted, chloroform extracted, ethanol precipitated and cut with the restriction enzymes BclI and XhoI. The restriction fragment was purified on an agarose gel and eluted.

This fragment was ligated to the cDNA cgbS2.1 that had been grown in dam$^-$ E. coli, cut with the restriction enzymes BclI and XhoI, and gel-purified using the Promega magic PCR kit. The resulting plasmid was sequenced to verify that cgbstop-2 contains the 3' portion of the cGB-PDE open reading frame.

Second, a plasmid carrying the 5' end of the human cGB-PDE open reading frame was generated. Its insert was generated by PCR using clone cgbS3.1 as a template. PCR was performed as described above using primers cgbmet156 and cgbS2.1A2 150.

Primer cgbmet156 (SEQ ID NO: 20) 5' TACAGAATTCT-GACCATGGAGCGGGCCGGC 3'

Primer cgbS2.1A2150 (SEQ ID NO: 21) 5' CATrCTAAGCGGATACAG 3'

The resulting PCR fragment was phenol/choloform extracted, choloform extracted, ethanol precipitated and purified on a Sepharose CL-6B column. The fragment was cut with the restriction enzymes EcoRV and EcoRI, run on an agarose gel and purified by spinning through glass wool. Following phenol/chloroform extraction, chloroform extraction and ethanol precipitation, the fragment was ligated into EcoRI/EcoRV digested BluescriptII SK(+) to generate plasmid cgbmet156. The DNA sequence of the insert and junctions was determined. The insert contains a new EcoRI site and an additional 5 nucleotides that together replace the original 155 nucleotides 5' of the initiation codon. The insert extends to an EcoRV site beginning 531 nucleotides from the initiation codon.

The 5' and 3' portions of the cGB-PDE open reading frame were then assembled in vector pBNY6a. The vector pBNY6a was cut with EcoRI and XhoI, isolated from a gel and combined with the agarose gel purified EcoRI/EcoRV fragment from cgbmet156 and the agarose gel purified EcoRV/XhoI fragment from cgbstop-2. The junctions of the insert were sequenced and the construct was named hcbgmet156-2 6a.

The cGB-PDE insert from hcbgmet156-2 6a was then moved into the expression vector pBNY6n. Expression of DNA inserted in this vector is directed from the yeast ADH1 promoter and terminator. The vector contains the yeast 2 micron origin of replication, the pUC19 origin of replication and an ampicillan resistance gene. Vector pBNY6n was cut with EcoRI and XhoI and gel-purified. The EcoRI/XhoI insert from hcgbmet156-2 6a was gel purified using Promega magic PCR columns and ligated into the cut pBNY6n. All new junctions in the resulting construct, hcgbmet156-2 6n, were sequenced. The DNA and deduced amino acid sequences of the insert of hcgbmet156-2 6n which encodes a composite human cGB-PDE is set out in SEQ ID NOs: 22 and 23. The insert extends from the first methionine in clone cgbS3.1 (nucleotide 156) to the stop codon (nucleotide 2781) in the composite cDNA. Because the methionine is the most 5' methionine in clone cgbS3.1 and because there are no stop codons in frame with the methionine and upstream of it, the insert in pBNY6n may represent a truncated form of the open reading frame.

Variant cDNAs

Four human cGB-PDE cDNAs that are different from the hcgbmet156-2 6n composite cDNA have been isolated. One cDNA, cgbL23.1, is missing an internal region of hcgbmet156-2 6n (nucleotides 997–1000 to 1444–1447). The exact end points of the deletion cannot be determined from the cDNA sequence at those positions. Three of the four variant cDNAs have 5' end sequences that diverge from the hcgbmet156-2 6n sequence upstream of nucleotide 151 (cDNAs cgbA7f, cgbA5C, cgbI2). These cDNAs presumably represent alteratively spliced or unspliced mRNAs.

EXAMPLE 7

The composite human cGB-PDE cDNA construct, hcgbmet156-2 6n, was transformed into the yeast strain YKS45 (ATCC 74225) (MATα his3 trp1 ura3 leu3 pde1::HIS3 pde2::TRP1) in which two endogenous PDE genes are deleted. Transformants complementing the leu⁻ deficiency of the YKS45 strain were selected and assayed for cGB-PDE activity. Extracts from cells bearing the plasmid hcgbmet156-2 6n were determined to display cyclic GMP-specific phosphodiesterase activity by the assay described below.

One liter of YKS45 cells transformed with the plasmid cgbmet156-2 6n and grown in SC-leu medium to a density of $1-2\times10^7$ cells/ml was harvested by centrifugation, washed once with deionized water, frozen in dry ice/ethanol and stored at −70° C. Cell pellets (1–1.5 ml) were thawed on ice in the presence of an equal volume of 25 mM Tris-Cl (pH 8.0)/5 mM EDTA/5 mM EGTA/1 mM o-phenanthroline/0.5 mM AEBSF (Calbiochem)/0.1% βg-mercaptoethanol and 10 ug/ml each of aprotinin, leupeptin, and pepstatin A. The thawed cells were added to 2 ml of acid-washed glass beads (425–600 μM, Sigma) in 15 ml Corex tube. Cells were broken with 4 cycles consisting of a 30 second vortexing on setting 1 followed by a 60 second incubation on ice. The cell lysate was centrifuged at 12,000×g for 10 minutes and the supernatant was passed through a 0.8μ filter. The supernatant was assayed for cGMP PDE activity as follows. Samples were incubated for 20 minutes at 30° C. in the presence of 45 mM Tris-Cl (pH 8.0), 2 mM EGTA, 1 mM EDTA, 0.2 mg/ml BSA, 5 mM $MgCl_2$, 0.2 mM o-phenanthroline, 2 ug/ml each of pepstatin A, leupeptin, and aprotinin, 0.1 mM AEBSF, 0.02% β-mercaptoethanol and 0.1 mM [$^3$H]cGMP as substrate. [$^{14}$C]-AMP (0.5 nCi/assay) was added as a recovery standard. The reaction was terminated with stop buffer (0.1M ethanolamine pH 9.0, 0.5M ammonium sulfate, 10 mM EDTA, 0.05% SDS final concentration). The product was separated from the cyclic nucleotide substrate by chromatography on BioRad Affi-Gel 601. The sample was applied to a column containing approximately 0.25 ml of Affi-Gel 601 equilibrated in column buffer (0.1M ethanolamine pH 9.0 containing 0.5M ammonium sulfate). The column was washed five times with 0.5 ml of column buffer. The product was eluted with four 0.5 ml aliquots of 0.25 acetic acid and mixed with 5 ml Ecolume (ICN Biochemicals). The radioactive product was measured by scintillation counting.

EXAMPLE 8

Analysis of expression of cGB-PDE mRNA in human tissues was carried out by RNase protection assay.

A probe corresponding to a portion of the putative cGMP binding domain of cGB-PDE (402 bp corresponding to nucleotides 1450 through 185 1 of SEQ ID NO: 13) was generated by PCR. The PCR fragment was inserted into the EcoRI site of the plasmid pBSII SK(−) to generate the plasmid RP3. RP3 plasmid DNA was linearized with XbaI and antisense probes were generated by a modification of the Stratagene T7 RNA polymerase kit. Twenty-five ng of linearized plasmid was combined with 20 microcuries of alpha $^{32}$p rUTP (800 Ci/mmol, 10 mCi/ml), 1× transcription buffer (40 mM TrisCl, pH 8, 8 mM $MgCl_2$, 2 mM spermidine, 50 mM NaCl), 0.25 mM each rATP, rGTP and rCTP, 0.1 units of RNase Block II, 5 mM DTT, 8 μM rUTP and 5 units of T7 RNA Polymerase in a total volume of 5 μl. The reaction was allowed to proceed 1 hour at room temperature and then the DNA template was removed by digestion with RNase free DNase. The reaction was diluted into 100 μl of 40 mM TrisCl, pH 8, 6 mM $MgCl_2$ and 10 mM NaCl. Five units of RNase-free DNase were added and the reaction was allowed to continue another 15 minutes at 37° C. The reaction was stopped by a phenol extraction followed by a phenol chloroform extraction. One half volume of 7.5M $NH_4OAc$ was added and the probe was ethanol precipitated.

The RNase protection assays were carried out using the Ambion RNase Protection kit (Austin, Tex.) and 10 μg RNA isolated from human tissues by an acid guanidinium extraction method. Expression of cGB-PDE mRNA was easily detected in RNA extracted from skeletal muscle, uterus, bronchus, skin, right saphenous vein, aorta and SW1088 glioblastoma cells. Barely detectable expression was found in RNA extracted from right atrium, right ventricle, kidney cortex, and kidney medulla. Only complete protection of the RP3 probe was seen. The lack of partial protection argues against the cDNA cgbL23.1 (a variant cDNA described in Example 7) representing a major transcript, at least in these RNA samples.

EXAMPLE 9

Polyclonal antisera was raised to E. coli-produced fragments of the human cGB-PDE.

A portion of the human cGB-PDE cDNA (nucleotides 1668–2612 of SEQ ID NO: 22, amino acids 515–819 of SEQ ID NO: 23) was amplified by PCR and inserted into the E. coli expression vector pGEX2T (Pharmacia) as a BamHI/EcoRI fragment. The pGEX2T plasmid carries an ampicillin resistance gene, an E. coli laq I$^q$ gene and a portion of the Schistosoma japonicum glutathione-S-transferase (GST) gene. DNA inserted in the plasmid can be expressed as a fusion protein with GST and can then be cleaved from the GST portion of the protein with thrombin. The resulting plasmid, designated cgbPE3, was transformed into E. coli strain LE392 (Stratagene). Transformed cells were grown at 37° C. to an OD600 of 0.6. IPTG (isopropylthioalactopyranoside) was added to 0.1 mM and the cells were grown at 37° C. for an additional 2 hours. The cells were collected by centrifugation and lysed by sonication. Cell debris was removed by centrifugation and the supernatant was fractionated by SDS-PAGE. The gel was stained with cold 0.4M KCl and the GST-cgb fusion protein band was excised and electroeluted. The PDE portion of the protein was separated from the GST portion by digestion with thrombin. The digest was fractionated by SDS-PAGE, the PDE protein was electroeluted and injected subcutaneously into a rabbit. The resultant antisera recognizes both the bovine cGB-PDE fragment that was utilized as antigen and the full length human cGB-PDE protein expressed in yeast (see Example 8).

EXAMPLE 10

Polynucleotides encoding various cGB-PDE analogs and cGB-PDE fragments were generated by standard methods.

A. cGB-PDE Analogs

All known cGMP-binding PDEs contain two internally homologous tandem repeats within their putative cGMP-binding domains. In the bovine cGB-PDE of the invention, the repeats span at least residues 228-311 (repeat A) and 410-500 (repeat B) of SEQ ID NO: 10. Site-directed mutagenesis of an aspartic acid that is conserved in repeats A and B of all known cGMP-binding PDEs was used to create analogs of cGB-PDE having either Asp-289 replaced with Ala (D289A) or Asp-478 replaced with Ala (D478A). Recombinant wild type (WT) bovine and mutant bovine cGB-PDEs were expressed in COS-7 cells. cGB-PDE purified from bovine lung (native cGB-PDE) and WT cGB-PDE displayed identical cGMP-binding kinetics with a $K_d$ of approximately 2 µM and a curvilinear dissociation profile ($t_{1/2}$=1.3 hours at 4° C.). This curvilinearity may have been due to the presence of distinct high affinity (slow) and low affinity (fast) sites of cGMP binding. The D289A mutant had significantly decreased affinity for cGMP ($K_d$>20 µM) and a single rate of cGMP-association ($t_{1/2}$=0.5 hours), that was similar to that calculated for the fast site of WT and native cGB-PDE. This suggested the loss of a slow cGMP-binding site in repeat A of this mutant. Conversely, the D478A mutant showed higher affinity for cGMP ($K_d$ of approximately 0.5 µM) and a single cGMP-dissociation rate ($t_{1/2}$= 2.8 hours) that was similar to the calculated rate of the slow site of WT and native cGB-PDE. This suggested the loss of a fast site when repeat B was modified. These results indicate that dimeric cGB-PDE possesses two homologous but kinetically distinct cGMP-binding sites, with the conserved aspartic acid being critical for interaction with cGMP at each site. See, Colbran et al., *FASEB J.*, 8: Abstract 2149 (May 15, 1994).

B. Amino-Terminal Truncated cGB-PDE Polypeptides

A truncated human cGB-PDE polypeptide including amino acids 516-875 of SEQ ID NO: 23 was expressed in yeast. A cDNA insert extending from the NcoI site at nucleotide 1555 of SEQ ID NO: 22 through the XhoI site at the 3' end of SEQ ID NO: 22 was inserted into the ADH2 yeast expression vector YEpC-PADH2d [Price et al., *Meth. Enzymol.*, 185:308-318 (1990)] that had been digested with NcoI and SalI to generate plasmid YEpC-PADH2d HcGB. The plasmid was transformed into spheroplasts of the yeast strain yBJ2-54 (prc1-407 prb1-1122 pep4-3 leu2 trp1 ura3-52 Apde1::URA3, HIS3 Apde2::TRP1 cir°). The endogenous PDE genes are deleted in this strain. Cells were grown in SC-leu media with 2% glucose to $10^7$ cells/ml, collected by filtration and grown 24 hours in YEP media containing 3% glycerol. Cells were pelleted by centrifugation and stored frozen. Cells were disrupted with glass beads and the cell homogenate was assayed for phosphodiesterase activity essentially as described in Prpic et al., *Anal. Biochem.*, 208:155-160 (1993). The truncated human cGB-PDE polypeptide exhibited phosphodiesterase activity.

C. Carboxy-Terminal Truncated cGB-PDE Polypeptides

Two different plasmids encoding carboxy-terminal truncated human cGB-PDE polypeptides were constructed.

Plasmid pBJ6-84Hin contains a cDNA encoding amino acids 1-494 of SEQ ID NO: 23 inserted into the NcoI and SalI sites of vector YEpC-PADI-I2d. The cDNA insert extends from the NcoI site at nucleotide position 10 of SEQ ID NO: 22 through the HindIII site at nucleotide position 1494 of SEQ ID NO: 22 followed by a linker and the SalI site of YEpC-PADH2d.

Plasmid pB16-84Ban contains a cDNA encoding amino acids 1-549 of SEQ ID NO: 23 inserted into the NcoI and SalI sites of vector YEpC-PADH2d. The cDNA insert extends from the NcoI site at nucleotide position 10 of SEQ ID NO: 22 through the BanI site at nucleotide position 1657 of SEQ ID NO: 22 followed by a linker and the SalI site of YEpC-PADH2d.

The trucated cGB-PDE polypeptides are useful for screening for modulators of cGB-PDE activity.

EXAMPLE 11

Monoclonal antibodies reactive with human cGB-PDE were generated.

Yeast yBJ2-54 containing the plasmid YEpADH2 HcGB (Example 10B) were fermented in a New Brunswick Scientific 10 liter Microferm. The cGB-PDE cDNA insert in plasmid YEpADH2 HcGB extends from the NcoI site at nucleotide 12 of SEQ ID NO: 22 to the XhoI site at the 3' end of SEQ ID NO: 22. An inoculum of $4 \times 10^9$ cells was added to 8 liters of media containing SC-leu, 595 glucose, trace metals, and trace vitamins. Fermentation was maintained at 26° C., agitated at 600 rpm with the standard microbial impeller, and aerated with compressed air at 10 volumes per minute. When glucose decreased to 0.3% at 24 hours post-inoculation the culture was infused with 2 liters of 5× YEP media containing 15% glycerol. At 66 hours pest-inoculation the yeast from the ferment was harvested by centrifugation at 4,000×g for 30 minutes at 4° C. Total yield of biomass from this fermentation approached 350 g wet weight.

Human cGB-PDE enzyme was purified from the yeast cell pellet. Assays for PDE activity using 1 mM cGMP as substrate was employed to follow the chromatography of the enzyme. All chromatographic manipulations were performed at 4° C.

Yeast (29 g wet weight) were resuspended in 70 ml of buffer A (25 mM Tris pH 8.0, 0.25 mM DTT, 5 mM MgCl$_2$, 10 µM ZnSO$^4$, 1 mM benzamidine) and lysed by passing through a microfluidizer at 22-24,000 psi. The lysate was centrifuged at 10,000×g for 30 minutes and the supernatant was applied to a 2.6× 28 cm column containing Pharmacia Fast Flow Q anion exchange resin equilibrated with buffer B containing 20 mM BisTris-propane pH 6.8, 0.25 mM DTT, 1 mM MgCl$_2$, and 10 µM ZnSO$_4$. The column was washed with 5 column volumes of buffer B containing 0.125M NaCl and then developed with a linear gradient from 0.125 to 1.0M NaCl. Fractions containing the enzyme were pooled and applied directly to a 5×20 cm column of ceramic hydroxyapatite (BioRad) equilibrated in buffer C containing 20 mM BisTris-propane pH 6.8, 0.25 mM DTT, 0.25 MKCl, 1 mM MgCl$_2$, and 10 µM ZnSO$_4$. The column was washed with 5 column volumes of buffer C and eluted with a linear gradient from 0 to 250 mM potassium phosphate in buffer C. The pooled enzyme was concentrated 8-fold by ultrafiltration (YM30 membrane, Amicon). The concentrated enzyme was chromatographed on a 2.6×90 cm column of Pharmacia Sephacryl S300 (Piscataway, N.J.) equilibrated in 25 mM BisTris-propane pH 6.8, 0.25 mM DTT, 0.25M NaCl, 1 mM MgCl$_2$, and 20 µM ZnSO$_4$. Approximately 4 mg of protein was obtained. The recombinant human cGB-PDE enzyme accounted for approximately 90% of protein obtained as judged by SDS polyacrylamide gel electrophoresis followed by Coomassie blue staining.

The purified protein was used as an antigen to raise monoclonal antibodies. Each of 19 week old Balb/c mice (Charles River Biotechnical Services, Inc., Wilmington, Mass.) was immunized sub-cutaneously with 50 ug purified human cGB-PDE enzyme in a 200 ul emulsion consisting of 50% Freund's complete adjuvant (Sigma Chemical Co.). Subsequent boosts on day 20 and day 43 were administered in incomplete Freund's adjuvant. A pre-fusion boost was done on day 86 using 50 ug enzyme in PBS. The fusion was performed on day 90.

The spleen from mouse #1817 was removed sterilely and placed in 10ml serum free RPMI 1640. A single-cell suspension was formed and filtered through sterile 70-mesh Nitex cell strainer (Becton Dickinson, Parsippany, N.J.), and washed twice by centrifuging at 200 g for 5 minutes and resuspending the pellet in 20 ml serum free RPMI. Thymocytes taken from 3 naive Balb/c mice were prepared in a similar manner.

NS-1 myeloma cells, kept in log phase in RPMI with 11% Fetalclone (FBS) (Hyclone Laboratories, Inc., Logan, Utah) for three days prior to fusion, were centrifuged at 200 g for 5 minutes, and the pellet was washed twice as described in the foregoing paragraph. After washing, each cell suspension was brought to a final volume of 10 ml in serum free RPMI, and 20 µl was diluted 1:50 in 1 ml serum free RPMI. 20 µl of each dilution was removed, mixed with 20 µl 0.4% trypan blue stain in 0.85% saline (Gibco), loaded onto a hemocytometer (Baxter Healthcare Corp., Deerfield, Ill.) and counted.

Two×$10^8$ spleen cells were combined with 4.0×$10^7$ NS-1 cells, centrifuged and the supernatant was aspirated. The cell pellet was dislodged by tapping the tube and 2 ml of 37° C. PEG 1500 (50% in 75 mM Hepes, pH 8.0) (Boehringer Mannheim) was added with stirring over the course of 1 minute, followed by adding 14 ml of serum free RPMI over 7 minutes. An additional 16 ml RPMI was added and the cells were centrifuged at 200 g for 10 minutes. After discarding the supernatant, the pellet was resuspended in 200 ml RPMI containing 15% FBS, 1130 µM sodium hypoxanthine, 0.4 µM aminopterin, 16 µM thyroidine (HAT) (Gibco), 25 units/ml IL-6 (Boehringer Mannheim) and 1.5× $10^6$ thymocytes/ml. The suspension was first placed in a T225 flask (Corning, United Kingdom) at 37° C. for two hours before being dispensed into ten 96-well flat bottom tissue culture plates (Corning, United Kingdom) at 200 µl/well. Cells in plates were fed on days 3, 4, 5 post fusion day by aspirating approximately 100 µl from each well with an 20 G needle (Beckton Dickinson), and adding 100 µl/well plating medium described above except containing 10 units/ml IL-6 and lacking thymocytes.

The fusion was screened initially by ELISA. Immulon 4 plates (Dynatech) were coated at 4° C. overnight with purified recombinant human cGB-PDE enzyme (100 ng/well in 50 mM carbonate buffer pH 9.6). The plates were washed 3× with PBS containing 0.05% Tween 20 (PBST). The supernatants from the individual hybridoma wells were added to the enzyme coated wells (50 µl/well). After incubation at 37° C. for 30 minutes, and washing as above, 50 µl of horseradish peroxidase conjugated goat anti-mouse IgG(fc) (Jackson ImmunoResearch, West Grove, Pa.) diluted 1:3500 in PBST was added. Plates were incubated as above, washed 4× with PBST and 100 µl substrate consisting of 1 mg/ml o-phenylene diamine (Sigma) and 0.1 µl/ml 30% $H_2O_2$ in 100 mM citrate, pH 4.5, was added. The color reaction was stopped in 5 minutes with the addition of 50 µl of 15% $H_2SO_4$. $A_{490}$ was read on a plate reader (Dynatech).

Wells C5G, E4D, F1G, F9H, F11G, J4A, and J5D were picked and renamed 102A, 102B, 102C, 102D, 102E, 102F, and 102G respectively, cloned two or three times, successively, by doubling dilution in RPMI, 15% FBS, 100 µM sodium hypoxanthine, 16 µM thymidine, and 10 units/ml IL-6. Wells of clone plates were scored visually after 4 days and the number of colonies in the least dense wells were recorded. Selected wells of the each cloning were tested by ELISA.

The monoclonal antibodies produced by above hybridomas were isotyped in an ELISA assay. Results showed that monoclonal antibodies 102A to 102E were IgG1, 102F was IgG2b and 102G was IgG2a.

All seven monoclonal antibodies reacted with human cGS-PDE as determined by Western analysis.

EXAMPLE 12

Developing modulators of the biological activities of specific PDEs requires differentiating PDE isozymes present in a particular assay preparation. The classical enzymological approach of isolating PDEs from natural tissue sources and studying each new isozyme is hampered by the limits of purification techniques and the inability to definitively assess whether complete resolution of a isozyme has been achieved. Another approach has been to identify assay conditions which might favor the contribution of one isozyme and minimize the contribution of others in a preparation. Still another approach has been the separation of PDEs by immunological means. Each of the foregoing approaches for differentiating PDE isozymes is time consuming and technically difficult. As a result many attempts to develop selective PDE modulators have been performed with preparations containing more than one isozyme. Moreover, PDE preparations from natural tissue sources are susceptible to limited proteolysis and may contain mixtures of active proteolytic products that have different kinetic, regulatory and physiological properties than the full length PDEs.

Recombinant cGB-PDE polypeptide products of the invention greatly facilitate the development of new and specific cGB-PDE modulators. The use of human recombinant enzymes for screening for modulators has many inherent advantages. The need for purification of an isozyme can be avoided by expressing it recombinantly in a host cell that lacks endogenous phosphodiesterase activity (e.g., yeast strain YKS45 deposited as ATCC 74225). Screening compounds against human protein avoids complications that often arise from screening against non-human protein where a compound optimized on a non-human protein may fail to be specific for or react with the human protein. For example, a single amino acid difference between the human and rodent $5HT_{1B}$ serotonin receptors accounts for the difference in binding of a compound to the receptors. [See Oskenberg et al., Nature, 360: 161–163 (1992)]. Once a compound that modulates the activity of the cGB-PDE is discovered, its selectivity can be evaluated by comparing its activity on the cGB-PDE to its activity on other PDE isozymes. Thus, the combination of the recombinant cGB-PDE products of the invention with other recombinant PDE products in a series of independent assays provides a system for developing selective modulators of cGB-PDE. Selective modulators may include, for example, antibodies and other proteins or peptides which specifically bind to the cGB-PDE or cGB-PDE nucleic acid, oligonucleotides which specifically bind to the cGB-PDE (see Patent Cooperation Treaty International Publication No. WO93/05182 published Mar. 18, 1993 which describes methods for selecting oligonucleotides which selectively bind to target biomolecules) or cGB-PDE nucleic acid (e.g., antisense oligonucleotides) and other non-peptide natural or synthetic compounds which specifically bind to the cGB-PDE or cGB-PDE nucleic acid. Mutant forms of the cGB-PDE which alter the enzymatic activity of the cGB-PDE or its localization in a cell are also contemplated. Crystallization of recombinant cGB-PDE alone and bound to a modulator, analysis of atomic structure by X-ray crystallography, and computer modelling of those structures are methods useful for designing and optimizing non-peptide selective modulators. See, for example, Erickson et at., *Ann. Rep. Med. Chem.*, 27:271–289 (1992) for a general review of structure-based drug design.

Targets for the development of selective modulators include, for example: (1) the regions of the cGB-PDE which contact other proteins and/or localize the cGB-PDE within a cell, (2) the regions of the cGB-PDE which bind substrate, (3) the allosteric cGMP-binding site(s) of cGB-PDE, (4) the metal-binding regions of the cGB-PDE, (5) the phosphorylation site(s) of cGB-PDE and (6) the regions of the cGB-PDE which are involved in dimerization of cGB-PDE subunits.

While the present invention has been described in terms of specific embodiments, it is understood that variations and modifications will occur to those skilled in the art. Accordingly, only such limitations as appear in the appended claims should be placed on the invention.

---

We claim:

1. A fragment of human cGMP-binding phosphodiesterase consisting of the amino acids 516 to 875 of SEQ ID NO: 23.

2. A fragment of human cGMP-binding phosphodiesterase consisting of the amino acids 1–494 of SEQ ID NO: 23.

3. A fragment of human cGMP-binding phosphodiesterase consisting of the amino acids 1–549 of SEQ ID NO: 23.

* * * * *

UNITED STATES PATENT AND TRADEMARK OFFICE
CERTIFICATE OF CORRECTION

PATENT NO. : 5,702,936
DATED : May 27, 1994
INVENTOR(S) : Beavo et al.

Page 1 of 1

It is certified that error appears in the above-identified patent and that said Letters Patent is hereby corrected as shown below:

Title page,
OTHER PUBLICATIONS, McAllister-Lucas et al., replace "Phosphodiestera" with -- Phosphodiesterase --.

Column 4,
Line 61, replace "stare or status" with -- state or states --.

Column 9,
Line 58, replace "liter" with -- titer --.

Column 12,
Line 51, replace "hexanueleotide" with -- hexanucleotide --.

Column 16,
Line 60, replace "done" with -- clone --.

Column 18,
Line 30, replace "phenol/choloform" with -- phenol/chloroform --.
Line 31, replace "choloform" with -- chloroform --.

Column 22,
Line 8, replace "trucated" with -- truncated --.
Line 27, replace "pest-inoculation" with -- post-inoculation --.

Signed and Sealed this

Sixteenth Day of April, 2002

Attest:

Attesting Officer

JAMES E. ROGAN
*Director of the United States Patent and Trademark Office*

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
  ( A ) LENGTH: 20 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:1:

Arg Glu Xaa Asp Ala Asn Arg Ile Asn Tyr Met Tyr Ala Gln Tyr Val
1               5                   10                  15

Lys Asn Thr Met
            20

( 2 ) INFORMATION FOR SEQ ID NO:2:

( i ) SEQUENCE CHARACTERISTICS:
  ( A ) LENGTH: 9 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:2:

Gln Ser Leu Ala Ala Ala Val Val Pro
1               5

( 2 ) INFORMATION FOR SEQ ID NO:3:

( i ) SEQUENCE CHARACTERISTICS:
  ( A ) LENGTH: 8 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:3:

Phe Asp Asn Asp Glu Gly Glu Gln
1               5

( 2 ) INFORMATION FOR SEQ ID NO:4:

( i ) SEQUENCE CHARACTERISTICS:
  ( A ) LENGTH: 23 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:4:

TTYGAYAAYG AYGARGGNGA RCA 23

( 2 ) INFORMATION FOR SEQ ID NO:5:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( i v ) ANTI-SENSE: YES ( x i ) SEQUENCE DESCRIPTION: SEQ ID NO:5:

AARCTRTTRC TRCTYCCNCT YGT 23

( 2 ) INFORMATION FOR SEQ ID NO:6:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

AAYTAYATGT AYGCNCARTA YGT 23

( 2 ) INFORMATION FOR SEQ ID NO:7:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( i v ) ANTI-SENSE: YES ( x i ) SEQUENCE DESCRIPTION: SEQ ID NO:7:

TTRATRTACA TRCGNGTYAT RCA 23

( 2 ) INFORMATION FOR SEQ ID NO:8:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA ( i v ) ANTI-SENSE: YES ( x i ) SEQUENCE DESCRIPTION: SEQ ID NO:8:

TTRATRTACA TRCGNGTYAT RCANTTYTTR TGNTAC 36

( 2 ) INFORMATION FOR SEQ ID NO:9:

( i ) SEQUENCE CHARACTERISTICS:
        ( A ) LENGTH: 4474 base pairs
        ( B ) TYPE: nucleic acid
        ( C ) STRANDEDNESS: single -continued ( D ) TOPOLOGY: linear ( i i ) MOLECULE TYPE: cDNA ( i x ) FEATURE:
    ( A ) NAME/KEY: CDS
    ( B ) LOCATION: 99..2723

( x i ) SEQUENCE DESCRIPTION: SEQ ID NO:9:

```
GGGAGGGTCT  CGAGGCGAGT  TCTGCTCCTC  GGAGGGAGGG  ACCCCAGCTG  GAGTGGAAAA                      60

CCAGCACCAG  CTGACCGCAG  AGACACGCCG  CGCTGATC ATG GAG AGG GCC GGC                            113
                                             Met Glu Arg Ala Gly
                                              1               5

CCC GGC TCC GCG CGG CCG CAA CAG CAA TGG GAC CAG GAC TCG GTC GAA                            161
Pro Gly Ser Ala Arg Pro Gln Gln Gln Trp Asp Gln Asp Ser Val Glu
             10                  15                  20

GCG TGG CTG GAC GAT CAC TGG GAC TTT ACC TTC TCT TAC TTT GTT AGG                            209
Ala Trp Leu Asp Asp His Trp Asp Phe Thr Phe Ser Tyr Phe Val Arg
                 25                  30                  35

AAA GGC ACC AGA GAA ATG GTC AAC GCA TGG TTT GCT GAG AGA GTT CAC                            257
Lys Gly Thr Arg Glu Met Val Asn Ala Trp Phe Ala Glu Arg Val His
         40                  45                  50

ACC ATT CCT GTG TGC AAG GAA GGA ATC AAG GGC CAC ACG GAA TCC TGC                            305
Thr Ile Pro Val Cys Lys Glu Gly Ile Lys Gly His Thr Glu Ser Cys
     55                  60                  65

TCT TGC CCC TTG CAG CCA AGT CCC CGT GCA GAG AGC AGT GTC CCT GGA                            353
Ser Cys Pro Leu Gln Pro Ser Pro Arg Ala Glu Ser Ser Val Pro Gly
 70                  75                  80                  85

ACA CCA ACC AGG AAG ATC TCT GCC TCT GAA TTC GAT CGG CCG CTT AGA                            401
Thr Pro Thr Arg Lys Ile Ser Ala Ser Glu Phe Asp Arg Pro Leu Arg
                 90                  95                 100

CCC ATC GTT ATC AAG GAT TCT GAG GGA ACT GTG AGC TTC CTC TCT GAC                            449
Pro Ile Val Ile Lys Asp Ser Glu Gly Thr Val Ser Phe Leu Ser Asp
            105                 110                 115

TCA GAC AAG AAG GAA CAG ATG CCT CTA ACC TCC CCA CGG TTT GAT AAT                            497
Ser Asp Lys Lys Glu Gln Met Pro Leu Thr Ser Pro Arg Phe Asp Asn
        120                 125                 130

GAT GAA GGG GAC CAG TGC TCG AGA CTC TTG GAA TTA GTG AAA GAT ATT                            545
Asp Glu Gly Asp Gln Cys Ser Arg Leu Leu Glu Leu Val Lys Asp Ile
    135                 140                 145

TCT AGT CAC TTG GAT GTC ACA GCC TTA TGT CAC AAA ATT TTC TTG CAC                            593
Ser Ser His Leu Asp Val Thr Ala Leu Cys His Lys Ile Phe Leu His
150                 155                 160                 165

ATC CAT GGA CTC ATC TCC GCC GAC CGC TAC TCC TTA TTC CTC GTC TGT                            641
Ile His Gly Leu Ile Ser Ala Asp Arg Tyr Ser Leu Phe Leu Val Cys
                170                 175                 180

GAG GAC AGC TCC AAC GAC AAG TTT CTT ATC AGC CGC CTC TTT GAT GTT                            689
Glu Asp Ser Ser Asn Asp Lys Phe Leu Ile Ser Arg Leu Phe Asp Val
            185                 190                 195

GCA GAA GGT TCA ACA CTG GAA GAA GCT TCA AAC AAC TGC ATC CGC TTA                            737
Ala Glu Gly Ser Thr Leu Glu Glu Ala Ser Asn Asn Cys Ile Arg Leu
        200                 205                 210

GAG TGG AAC AAA GGC ATC GTG GGA CAC GTG GCC GCT TTT GGC GAG CCC                            785
Glu Trp Asn Lys Gly Ile Val Gly His Val Ala Ala Phe Gly Glu Pro
    215                 220                 225

TTG AAC ATC AAA GAC GCC TAT GAG GAT CCT CGA TTC AAT GCA GAA GTT                            833
Leu Asn Ile Lys Asp Ala Tyr Glu Asp Pro Arg Phe Asn Ala Glu Val
230                 235                 240                 245

GAC CAA ATT ACA GGC TAC AAG ACA CAA AGT ATT CTT TGT ATG CCA ATT                            881
Asp Gln Ile Thr Gly Tyr Lys Thr Gln Ser Ile Leu Cys Met Pro Ile
                250                 255                 260
```

```
AAG AAT CAT AGG GAA GAG GTT GTT GGT GTA GCC CAG GCC ATC AAC AAG      929
Lys Asn His Arg Glu Glu Val Val Gly Val Ala Gln Ala Ile Asn Lys
            265                 270                 275

AAA TCA GGA AAT GGT GGG ACA TTC ACT GAA AAA GAC GAA AAG GAC TTT      977
Lys Ser Gly Asn Gly Gly Thr Phe Thr Glu Lys Asp Glu Lys Asp Phe
        280                 285                 290

GCT GCT TAC TTG GCA TTT TGT GGA ATT GTT CTT CAT AAT GCT CAA CTC     1025
Ala Ala Tyr Leu Ala Phe Cys Gly Ile Val Leu His Asn Ala Gln Leu
    295                 300                 305

TAT GAG ACT TCA CTG CTG GAG AAC AAG AGA AAT CAG GTG CTG CTT GAC     1073
Tyr Glu Thr Ser Leu Leu Glu Asn Lys Arg Asn Gln Val Leu Leu Asp
310                 315                 320                 325

CTT GCT AGC TTA ATT TTT GAA GAA CAA CAA TCA TTA GAA GTA ATT CTA     1121
Leu Ala Ser Leu Ile Phe Glu Glu Gln Gln Ser Leu Glu Val Ile Leu
                330                 335                 340

AAG AAA ATA GCT GCC ACT ATT ATC TCT TTC ATG CAG GTG CAG AAA TGC     1169
Lys Lys Ile Ala Ala Thr Ile Ile Ser Phe Met Gln Val Gln Lys Cys
            345                 350                 355

ACC ATT TTC ATA GTG GAT GAA GAT TGC TCC GAT TCT TTT TCT AGT GTG     1217
Thr Ile Phe Ile Val Asp Glu Asp Cys Ser Asp Ser Phe Ser Ser Val
        360                 365                 370

TTT CAC ATG GAG TGT GAG GAA TTA GAA AAA TCG TCA GAT ACT TTA ACA     1265
Phe His Met Glu Cys Glu Glu Leu Glu Lys Ser Ser Asp Thr Leu Thr
    375                 380                 385

CGG GAA CGT GAT GCA AAC AGA ATC AAT TAC ATG TAT GCT CAG TAT GTC     1313
Arg Glu Arg Asp Ala Asn Arg Ile Asn Tyr Met Tyr Ala Gln Tyr Val
390                 395                 400                 405

AAA AAT ACC ATG GAA CCA CTT AAT ATC CCA GAC GTC AGT AAG GAC AAA     1361
Lys Asn Thr Met Glu Pro Leu Asn Ile Pro Asp Val Ser Lys Asp Lys
                410                 415                 420

AGA TTT CCC TGG ACA AAT GAA AAC ATG GGA AAT ATA AAC CAG CAG TGC     1409
Arg Phe Pro Trp Thr Asn Glu Asn Met Gly Asn Ile Asn Gln Gln Cys
            425                 430                 435

ATT AGA AGT TTG CTT TGT ACA CCT ATA AAA AAT GGA AAG AAG AAC AAA     1457
Ile Arg Ser Leu Leu Cys Thr Pro Ile Lys Asn Gly Lys Lys Asn Lys
        440                 445                 450

GTG ATA GGG GTT TGC CAA CTT GTT AAT AAG ATG GAG GAA ACC ACT GGC     1505
Val Ile Gly Val Cys Gln Leu Val Asn Lys Met Glu Glu Thr Thr Gly
    455                 460                 465

AAA GTT AAG GCT TTC AAC CGC AAC GAT GAA CAG TTT CTG GAA GCT TTC     1553
Lys Val Lys Ala Phe Asn Arg Asn Asp Glu Gln Phe Leu Glu Ala Phe
470                 475                 480                 485

GTC ATC TTT TGT GGC TTG GGG ATC CAG AAC ACA CAG ATG TAC GAA GCA     1601
Val Ile Phe Cys Gly Leu Gly Ile Gln Asn Thr Gln Met Tyr Glu Ala
                490                 495                 500

GTG GAG AGA GCC ATG GCC AAG CAA ATG GTC ACG TTA GAG GTT CTG TCT     1649
Val Glu Arg Ala Met Ala Lys Gln Met Val Thr Leu Glu Val Leu Ser
            505                 510                 515

TAT CAT GCT TCA GCT GCA GAG GAA GAA ACC AGA GAG CTG CAG TCC TTA     1697
Tyr His Ala Ser Ala Ala Glu Glu Glu Thr Arg Glu Leu Gln Ser Leu
        520                 525                 530

GCG GCT GCT GTG GTA CCA TCT GCC CAG ACC CTT AAA ATC ACT GAC TTC     1745
Ala Ala Ala Val Val Pro Ser Ala Gln Thr Leu Lys Ile Thr Asp Phe
    535                 540                 545

AGC TTC AGC GAC TTT GAG CTG TCT GAC CTG GAA ACA GCA CTG TGC ACA     1793
Ser Phe Ser Asp Phe Glu Leu Ser Asp Leu Glu Thr Ala Leu Cys Thr
550                 555                 560                 565

ATC CGG ATG TTC ACT GAC CTC AAC CTT GTG CAG AAC TTC CAG ATG AAA     1841
Ile Arg Met Phe Thr Asp Leu Asn Leu Val Gln Asn Phe Gln Met Lys
                570                 575                 580
```

| | | | | | | | | | | | | | | | | |
|---|---|---|---|---|---|---|---|---|---|---|---|---|---|---|---|---|
| CAT | GAG | GTC | CTT | TGC | AAG | TGG | ATT | TTA | AGT | GTG | AAG | AAG | AAC | TAT | CGG | 1889 |
| His | Glu | Val | Leu | Cys | Lys | Trp | Ile | Leu | Ser | Val | Lys | Lys | Asn | Tyr | Arg | |
| | | | 585 | | | | | 590 | | | | | 595 | | | |
| AAG | AAC | GTC | GCC | TAT | CAT | AAT | TGG | AGA | CAT | GCC | TTT | AAT | ACA | GCT | CAG | 1937 |
| Lys | Asn | Val | Ala | Tyr | His | Asn | Trp | Arg | His | Ala | Phe | Asn | Thr | Ala | Gln | |
| | | 600 | | | | | 605 | | | | | 610 | | | | |
| TGC | ATG | TTT | GCG | GCA | CTA | AAA | GCA | GGC | AAA | ATT | CAG | AAG | AGG | CTG | ACG | 1985 |
| Cys | Met | Phe | Ala | Ala | Leu | Lys | Ala | Gly | Lys | Ile | Gln | Lys | Arg | Leu | Thr | |
| | 615 | | | | | 620 | | | | | 625 | | | | | |
| GAC | CTG | GAG | ATA | CTT | GCA | CTG | CTG | ATT | GCT | GCC | TTA | AGC | CAT | GAT | CTG | 2033 |
| Asp | Leu | Glu | Ile | Leu | Ala | Leu | Leu | Ile | Ala | Ala | Leu | Ser | His | Asp | Leu | |
| 630 | | | | | 635 | | | | | 640 | | | | | 645 | |
| GAT | CAC | CGT | GGT | GTC | AAT | AAC | TCA | TAC | ATA | CAG | CGA | AGT | GAA | CAC | CCA | 2081 |
| Asp | His | Arg | Gly | Val | Asn | Asn | Ser | Tyr | Ile | Gln | Arg | Ser | Glu | His | Pro | |
| | | | | 650 | | | | | 655 | | | | | 660 | | |
| CTT | GCT | CAG | CTC | TAC | TGC | CAT | TCA | ATC | ATG | GAG | CAT | CAT | CAT | TTT | GAT | 2129 |
| Leu | Ala | Gln | Leu | Tyr | Cys | His | Ser | Ile | Met | Glu | His | His | His | Phe | Asp | |
| | | | | 665 | | | | | 670 | | | | | 675 | | |
| CAG | TGC | CTG | ATG | ATC | CTT | AAT | AGT | CCT | GGC | AAT | CAG | ATT | CTC | AGT | GGC | 2177 |
| Gln | Cys | Leu | Met | Ile | Leu | Asn | Ser | Pro | Gly | Asn | Gln | Ile | Leu | Ser | Gly | |
| | | | 680 | | | | | 685 | | | | | 690 | | | |
| CTC | TCC | ATT | GAA | GAG | TAT | AAG | ACC | ACC | CTG | AAG | ATC | ATC | AAG | CAA | GCT | 2225 |
| Leu | Ser | Ile | Glu | Glu | Tyr | Lys | Thr | Thr | Leu | Lys | Ile | Ile | Lys | Gln | Ala | |
| | | 695 | | | | | 700 | | | | | 705 | | | | |
| ATT | TTA | GCC | ACA | GAC | CTA | GCA | CTG | TAC | ATA | AAG | AGA | CGA | GGA | GAA | TTT | 2273 |
| Ile | Leu | Ala | Thr | Asp | Leu | Ala | Leu | Tyr | Ile | Lys | Arg | Arg | Gly | Glu | Phe | |
| 710 | | | | | 715 | | | | | 720 | | | | | 725 | |
| TTT | GAA | CTT | ATA | ATG | AAA | AAT | CAA | TTC | AAT | TTG | GAA | GAT | CCT | CAT | CAA | 2321 |
| Phe | Glu | Leu | Ile | Met | Lys | Asn | Gln | Phe | Asn | Leu | Glu | Asp | Pro | His | Gln | |
| | | | | 730 | | | | | 735 | | | | | 740 | | |
| AAG | GAG | TTG | TTT | TTA | GCG | ATG | CTG | ATG | ACA | GCT | TGT | GAT | CTT | TCT | GCA | 2369 |
| Lys | Glu | Leu | Phe | Leu | Ala | Met | Leu | Met | Thr | Ala | Cys | Asp | Leu | Ser | Ala | |
| | | | 745 | | | | | 750 | | | | | 755 | | | |
| ATT | ACA | AAA | CCC | TGG | CCT | ATT | CAA | CAA | CGG | ATA | GCA | GAA | CTT | GTT | GCC | 2417 |
| Ile | Thr | Lys | Pro | Trp | Pro | Ile | Gln | Gln | Arg | Ile | Ala | Glu | Leu | Val | Ala | |
| | | 760 | | | | | 765 | | | | | 770 | | | | |
| ACT | GAA | TTT | TTT | GAC | CAA | GGA | GAT | AGA | GAG | AGG | AAA | GAA | CTC | AAC | ATA | 2465 |
| Thr | Glu | Phe | Phe | Asp | Gln | Gly | Asp | Arg | Glu | Arg | Lys | Glu | Leu | Asn | Ile | |
| 775 | | | | | 780 | | | | | 785 | | | | | | |
| GAG | CCC | GCT | GAT | CTA | ATG | AAC | CGG | GAG | AAG | AAA | AAC | AAA | ATC | CCA | AGT | 2513 |
| Glu | Pro | Ala | Asp | Leu | Met | Asn | Arg | Glu | Lys | Lys | Asn | Lys | Ile | Pro | Ser | |
| 790 | | | | | 795 | | | | | 800 | | | | | 805 | |
| ATG | CAA | GTT | GGA | TTC | ATA | GAT | GCC | ATC | TGC | TTG | CAA | CTG | TAT | GAG | GCC | 2561 |
| Met | Gln | Val | Gly | Phe | Ile | Asp | Ala | Ile | Cys | Leu | Gln | Leu | Tyr | Glu | Ala | |
| | | | | 810 | | | | | 815 | | | | | 820 | | |
| TTG | ACC | CAT | GTG | TCG | GAG | GAC | TGT | TTC | CCT | TTG | CTG | GAC | GGC | TGC | AGA | 2609 |
| Leu | Thr | His | Val | Ser | Glu | Asp | Cys | Phe | Pro | Leu | Leu | Asp | Gly | Cys | Arg | |
| | | | 825 | | | | | 830 | | | | | 835 | | | |
| AAG | AAC | AGG | CAG | AAA | TGG | CAG | GCT | CTT | GCA | GAA | CAG | CAG | GAG | AAG | ACA | 2657 |
| Lys | Asn | Arg | Gln | Lys | Trp | Gln | Ala | Leu | Ala | Glu | Gln | Gln | Glu | Lys | Thr | |
| | | 840 | | | | | 845 | | | | | 850 | | | | |
| CTG | ATC | AAT | GGT | GAA | AGC | AGC | CAG | ACC | AAC | CGA | CAG | CAA | CGG | AAT | TCC | 2705 |
| Leu | Ile | Asn | Gly | Glu | Ser | Ser | Gln | Thr | Asn | Arg | Gln | Gln | Arg | Asn | Ser | |
| 855 | | | | | 860 | | | | | 865 | | | | | | |
| GTT | GCT | GTC | GGG | ACA | GTG | TAGCCAGGTG | TATCAGATGA | GTGAGTGTGT | | | | | | | | 2753 |
| Val | Ala | Val | Gly | Thr | Val | | | | | | | | | | | |
| 870 | | | | | 875 | | | | | | | | | | | |

GCTCAGCTCA GTCCTCTGCA ACACCATGAA GCTAGGCATT CCAGCTTAAT TCCTGCAGTT    2813

GACTTTAAAA AACTGGCATA AAGCACTAGT CAGCATCTAG TTCTAGCTTG ACCAGTGAAG    2873

-continued

| | | | | | |
|---|---|---|---|---|---|
| AGTAGAACAC | CACCACAGTC | AGGGTGCAGA | GCAGTTGGCA | GTCTCCTTTC | GAACCCAGAC | 2933 |
| TGGTGAATTT | AAAGAAGAGC | AGTCGTCGTT | TATATCTCTG | TCTTTTCCTA | AGCGGGGTGT | 2993 |
| GGAATCTCTA | AGAGGAGAGA | GAGATCTGGA | CCACAGGTCC | AATGCGCTCT | GTCCTCTCAG | 3053 |
| CTGCTTCCCC | CACTGTGCTG | TGACCTCTCA | ATCTGAGAAA | CGTGTAAGGA | AGGTTTCAGC | 3113 |
| GAATTCCCTT | TAAAATGTGT | CAGACAGTAG | CTTCTTGGGC | CGGGTTGTTC | CCGCAGCTCC | 3173 |
| CCATCTGTTT | GTTGTCTATC | TTGGCTGAAA | GAGGCTTTGC | TGTACCTGCC | ACACTCTCCT | 3233 |
| GGATCCCTGT | CCAGTAGCTG | ATCAAAAAAA | AGGATGTGAA | ATTCTCGTGT | GACTTTTTAG | 3293 |
| AAAAGGAAAG | TGACCCCGAG | GATCGGTGTG | GATTCACTAG | TTGTCCACAG | ATGATCTGTT | 3353 |
| TAGTTTCTAG | AATTTTCCAA | GATGATACAC | TCCTCCCTAG | TCTAGGGGTC | AGACCCTGTA | 3413 |
| TGGTGGCTGT | GACCCTTGAG | GAACTTCTCT | CTTTGCATGA | CATTAGCCAT | AGAACTGTTC | 3473 |
| TTGTCCAAAT | ACACAGCTCA | TATGCAGCTT | GCAGGAAACA | CTTTAAAAAC | ACAACTATCA | 3533 |
| CCTATGTTAT | TCTGATTACA | GAAGTTATCC | CTACTCACTG | TAAACATAAA | CAAAGCCCCC | 3593 |
| CAAACTTCAA | ATAGTTGTGT | GTGGTGAGAA | ACTGCAAGTT | TTCATCTCCA | GAGATAGCTA | 3653 |
| TAGGTAATAA | GTGGGATGTT | TCTGAAACTT | TTAAAAATAA | TCTTTTACAT | ATATGTTAAC | 3713 |
| TGTTTTCTTA | TGAGCACTAT | GGTTTGTTTT | TTTTTTTTTT | TGCTCTGCTT | TGACTTGCCC | 3773 |
| TTTTCACTCA | ATTATCTTGG | CAGTTTTTCT | AAATGACTTG | CACAGACTTC | TCCTGTACTT | 3833 |
| CATGGCTGTG | CAGTGTTCCA | TGCTGTGAGG | GCACCATCGT | GTATTAAATC | AGTTCCCTGG | 3893 |
| TCACACATAG | GTGAGCTGGT | TGGAAATTTT | TACCATTAAA | AAACCACTTT | CCCACATTGA | 3953 |
| TGCTTTCTAA | TCTGGCACAG | GATGCTTCTT | TTTTTCCCCT | TTTTCTCTGT | TTAATTATTG | 4013 |
| GAAATGGGAT | CTGTGGGATC | CTCGTTCCCT | GGCACCTAGC | TGCTCTCAAC | GTGGCCTGTG | 4073 |
| GCCAGCAGCA | TTGGCTAGAC | CTGGGGGCTT | GTTGGGAACG | GAGACCCTCT | GCCCTGCCCC | 4133 |
| TGGCCTGCTG | ACAAGGACCT | GCATTTTGCT | GAGCTCCAG | TGACCCTGGT | GTTTAATTGT | 4193 |
| TAACCATTGA | AAAAAATCAA | ACTATAGTTT | ATTTACAATG | TTGTGTTAAT | TTCGGGTGTA | 4253 |
| CAGCAAAGTG | ACTCAGTGGT | CAAGTACATT | TAAAACACTG | GGCATACTCT | CTCCCTCTCC | 4313 |
| TTGTGTACCT | GGTTGGTATT | TCCAGAAACC | ATGCTCTTGT | CTGTCCTGTA | GTTTTGGAAG | 4373 |
| CGCTTTCTCT | TTGAAGACTG | CCTTCTCTCC | TCTGTCTGCC | CTACATGGAC | TAGTTCGTTT | 4433 |
| ATTGTCCTAC | ATGGCTTTGC | TTCCATGTTC | CTCTCAACTT | T | | 4474 |

( 2 ) INFORMATION FOR SEQ ID NO:10:

( i ) SEQUENCE CHARACTERISTICS:
        ( A ) LENGTH: 875 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Met  Glu  Arg  Ala  Gly  Pro  Gly  Ser  Ala  Arg  Pro  Gln  Gln  Gln  Trp  Asp
 1                 5                      10                     15

Gln  Asp  Ser  Val  Glu  Ala  Trp  Leu  Asp  His  Trp  Asp  Phe  Thr  Phe
               20                      25                     30

Ser  Tyr  Phe  Val  Arg  Lys  Gly  Thr  Arg  Glu  Met  Val  Asn  Ala  Trp  Phe
          35                      40                     45

Ala  Glu  Arg  Val  His  Thr  Ile  Pro  Val  Cys  Lys  Glu  Gly  Ile  Lys  Gly
     50                      55                     60

His  Thr  Glu  Ser  Cys  Ser  Cys  Pro  Leu  Gln  Pro  Ser  Pro  Arg  Ala  Glu
65                      70                     75                     80
```

| | | | | | | | | | | | | | | |
|---|---|---|---|---|---|---|---|---|---|---|---|---|---|---|
|Ser|Ser|Val|Pro|Gly<br>85|Thr|Pro|Thr|Arg|Lys<br>90|Ile|Ser|Ala|Ser|Glu<br>95|Phe|
|Asp|Arg|Pro|Leu|Arg<br>100|Pro|Ile|Val|Ile|Lys<br>105|Asp|Ser|Glu|Gly<br>110|Thr|Val|
|Ser|Phe|Leu|Ser<br>115|Asp|Ser|Asp|Lys|Lys<br>120|Glu|Gln|Met|Pro<br>125|Leu|Thr|Ser|
|Pro|Arg<br>130|Phe|Asp|Asn|Asp|Glu<br>135|Gly|Asp|Gln|Cys|Ser<br>140|Arg|Leu|Leu|Glu|
|Leu<br>145|Val|Lys|Asp|Ile|Ser<br>150|Ser|His|Leu|Asp|Val<br>155|Thr|Ala|Leu|Cys|His<br>160|
|Lys|Ile|Phe|Leu|His<br>165|Ile|His|Gly|Leu|Ile<br>170|Ser|Ala|Asp|Arg|Tyr<br>175|Ser|
|Leu|Phe|Leu|Val<br>180|Cys|Glu|Asp|Ser|Ser<br>185|Asn|Asp|Lys|Phe|Leu<br>190|Ile|Ser|
|Arg|Leu|Phe<br>195|Asp|Val|Ala|Glu|Gly<br>200|Ser|Thr|Leu|Glu|Glu<br>205|Ala|Ser|Asn|
|Asn|Cys<br>210|Ile|Arg|Leu|Glu|Trp<br>215|Asn|Lys|Gly|Ile|Val<br>220|Gly|His|Val|Ala|
|Ala<br>225|Phe|Gly|Glu|Pro|Leu<br>230|Asn|Ile|Lys|Asp|Ala<br>235|Tyr|Glu|Asp|Pro|Arg<br>240|
|Phe|Asn|Ala|Glu|Val<br>245|Asp|Gln|Ile|Thr|Gly<br>250|Tyr|Lys|Thr|Gln|Ser<br>255|Ile|
|Leu|Cys|Met|Pro<br>260|Ile|Lys|Asn|His|Arg<br>265|Glu|Glu|Val|Val|Gly<br>270|Val|Ala|
|Gln|Ala|Ile<br>275|Asn|Lys|Lys|Ser|Gly<br>280|Asn|Gly|Gly|Thr|Phe<br>285|Thr|Glu|Lys|
|Asp|Glu<br>290|Lys|Asp|Phe|Ala|Ala<br>295|Tyr|Leu|Ala|Phe|Cys<br>300|Gly|Ile|Val|Leu|
|His<br>305|Asn|Ala|Gln|Leu|Tyr<br>310|Glu|Thr|Ser|Leu|Leu<br>315|Glu|Asn|Lys|Arg|Asn<br>320|
|Gln|Val|Leu|Leu|Asp<br>325|Leu|Ala|Ser|Leu|Ile<br>330|Phe|Glu|Glu|Gln|Gln<br>335|Ser|
|Leu|Glu|Val|Ile<br>340|Leu|Lys|Lys|Ile|Ala<br>345|Ala|Thr|Ile|Ile|Ser<br>350|Phe|Met|
|Gln|Val|Gln|Lys<br>355|Cys|Thr|Ile|Phe|Ile<br>360|Val|Asp|Glu|Asp<br>365|Cys|Ser|Asp|
|Ser|Phe<br>370|Ser|Ser|Val|Phe|His<br>375|Met|Glu|Cys|Glu|Glu<br>380|Leu|Glu|Lys|Ser|
|Ser<br>385|Asp|Thr|Leu|Thr|Arg<br>390|Glu|Arg|Asp|Ala|Asn<br>395|Arg|Ile|Asn|Tyr|Met<br>400|
|Tyr|Ala|Gln|Tyr|Val<br>405|Lys|Asn|Thr|Met|Glu<br>410|Pro|Leu|Asn|Ile|Pro<br>415|Asp|
|Val|Ser|Lys|Asp<br>420|Lys|Arg|Phe|Pro|Trp<br>425|Thr|Asn|Glu|Asn|Met<br>430|Gly|Asn|
|Ile|Asn|Gln<br>435|Gln|Cys|Ile|Arg|Ser<br>440|Leu|Leu|Cys|Thr|Pro<br>445|Ile|Lys|Asn|
|Gly|Lys<br>450|Lys|Asn|Lys|Val|Ile<br>455|Gly|Val|Cys|Gln|Leu<br>460|Val|Asn|Lys|Met|
|Glu|Glu<br>465|Thr|Thr|Gly|Lys<br>470|Val|Lys|Ala|Phe|Asn<br>475|Arg|Asn|Asp|Glu|Gln<br>480|
|Phe|Leu|Glu|Ala|Phe<br>485|Val|Ile|Phe|Cys|Gly<br>490|Leu|Gly|Ile|Gln|Asn<br>495|Thr|
|Gln|Met|Tyr|Glu|Ala|Val|Glu|Arg|Ala|Met|Ala|Lys|Gln|Met|Val|Thr|

|         |         |         | 500     |         |         | 505     |         |         |         | 510     |         |         |
|---------|---------|---------|---------|---------|---------|---------|---------|---------|---------|---------|---------|---------|

Leu Glu Val Leu Ser Tyr His Ala Ser Ala Ala Glu Glu Thr Arg
                515                 520                 525

Glu Leu Gln Ser Leu Ala Ala Ala Val Val Pro Ser Ala Gln Thr Leu
    530                 535                 540

Lys Ile Thr Asp Phe Ser Phe Ser Asp Phe Glu Leu Ser Asp Leu Glu
545                 550                 555                 560

Thr Ala Leu Cys Thr Ile Arg Met Phe Thr Asp Leu Asn Leu Val Gln
                565                 570                 575

Asn Phe Gln Met Lys His Glu Val Leu Cys Lys Trp Ile Leu Ser Val
            580                 585                 590

Lys Lys Asn Tyr Arg Lys Asn Val Ala Tyr His Asn Trp Arg His Ala
        595                 600                 605

Phe Asn Thr Ala Gln Cys Met Phe Ala Ala Leu Lys Ala Gly Lys Ile
    610                 615                 620

Gln Lys Arg Leu Thr Asp Leu Glu Ile Leu Ala Leu Leu Ile Ala Ala
625                 630                 635                 640

Leu Ser His Asp Leu Asp His Arg Gly Val Asn Asn Ser Tyr Ile Gln
                645                 650                 655

Arg Ser Glu His Pro Leu Ala Gln Leu Tyr Cys His Ser Ile Met Glu
            660                 665                 670

His His His Phe Asp Gln Cys Leu Met Ile Leu Asn Ser Pro Gly Asn
        675                 680                 685

Gln Ile Leu Ser Gly Leu Ser Ile Glu Glu Tyr Lys Thr Thr Leu Lys
    690                 695                 700

Ile Ile Lys Gln Ala Ile Leu Ala Thr Asp Leu Ala Leu Tyr Ile Lys
705                 710                 715                 720

Arg Arg Gly Glu Phe Phe Glu Leu Ile Met Lys Asn Gln Phe Asn Leu
                725                 730                 735

Glu Asp Pro His Gln Lys Glu Leu Phe Leu Ala Met Leu Met Thr Ala
            740                 745                 750

Cys Asp Leu Ser Ala Ile Thr Lys Pro Trp Pro Ile Gln Gln Arg Ile
        755                 760                 765

Ala Glu Leu Val Ala Thr Glu Phe Phe Asp Gln Gly Asp Arg Glu Arg
    770                 775                 780

Lys Glu Leu Asn Ile Glu Pro Ala Asp Leu Met Asn Arg Glu Lys Lys
785                 790                 795                 800

Asn Lys Ile Pro Ser Met Gln Val Gly Phe Ile Asp Ala Ile Cys Leu
                805                 810                 815

Gln Leu Tyr Glu Ala Leu Thr His Val Ser Glu Asp Cys Phe Pro Leu
            820                 825                 830

Leu Asp Gly Cys Arg Lys Asn Arg Gln Lys Trp Gln Ala Leu Ala Glu
        835                 840                 845

Gln Gln Glu Lys Thr Leu Ile Asn Gly Glu Ser Ser Gln Thr Asn Arg
    850                 855                 860

Gln Gln Arg Asn Ser Val Ala Val Gly Thr Val
865                 870                 875

( 2 ) INFORMATION FOR SEQ ID NO:11:

( i ) SEQUENCE CHARACTERISTICS:
        ( A ) LENGTH: 2060 base pairs
        ( B ) TYPE: nucleic acid
        ( C ) STRANDEDNESS: single
        ( D ) TOPOLOGY: linear (i i) MOLECULE TYPE: cDNA (x i) SEQUENCE DESCRIPTION: SEQ ID NO:11:

| | | | | | |
|---|---|---|---|---|---|
| GCGGCCGCGC | TCCGGCCGCT | TTGTCGAAAG | CCGGCCCGAC | TGGAGCAGGA | CGAAGGGGGA | 60 |
| GGGTCTCGAG | GCCGAGTCCT | GTTCTTCTGA | GGGACGGACC | CCAGCTGGGG | TGGAAAAGCA | 120 |
| GTACCAGAGA | GCCTCCGAGG | CGCGCGGTGC | CAACCATGGA | GCGGCCGGC | CCCAGCTTCG | 180 |
| GGCAGCAGCG | ACAGCAGCAG | CAGCCCCAGC | AGCAGAAGCA | GCAGCAGAGG | GATCAGGACT | 240 |
| CGGTCGAAGC | ATGGCTGGAC | GATCACTGGG | ACTTTACCTT | CTCATACTTT | GTTAGAAAAG | 300 |
| CCACCAGAGA | AATGGTCAAT | GCATGGTTTG | CTGAGAGAGT | TCACACCATC | CCTGTGTGCA | 360 |
| AGGAAGGTAT | CAGAGGCCAC | ACCGAATCTT | GCTCTTGTCC | CTTGCAGCAG | AGTCCTCGTG | 420 |
| CAGATAACAG | TGTCCCTGGA | ACACCAACCA | GGAAAATCTC | TGCCTCTGAA | TTTGACCGGC | 480 |
| CTCTTAGACC | CATTGTTGTC | AAGGATTCTG | AGGGAACTGT | GAGCTTCCTC | TCTGACTCAG | 540 |
| AAAAGAAGGA | ACAGATGCCT | CTAACCCCTC | CAAGGTTTGA | TCATGATGAA | GGGGACCAGT | 600 |
| GCTCAAGACT | CTTGGAATTA | GTGAAGGATA | TTTCTAGTCA | TTTGGATGTC | ACAGCCTTAT | 660 |
| GTCACAAAAT | TTCTTGCAT | ATCCATGGAC | TGATATCTGC | TGACCGCTAT | TCCCTGTTCC | 720 |
| TTGTCTGTGA | AGACAGCTCC | AATGACAAGT | TCTTATCAG | CCGCCTCTTT | GATGTTGCTG | 780 |
| AAGGTTCAAC | ACTGGAAGAA | GTTTCAAATA | ACTGTATCCG | CTTAGAATGG | AACAAAGGCA | 840 |
| TTGTGGACA | TGTGGCAGCG | CTTGGTGAGC | CCTTGAACAT | CAAAGATGCA | TATGAGGATC | 900 |
| CTCGGTTCAA | TGCAGAAGTT | GACCAAATTA | CAGGCTACAA | GACACAAAGC | ATTCTTTGTA | 960 |
| TGCCAATTAA | GAATCATAGG | GAAGAGGTTG | TTGGTGTAGC | CCAGGCCATC | AACAAGAAAT | 1020 |
| CAGGAAACGG | TGGGACATTT | ACTGAAAAAG | ATGAAAAGGA | CTTTGCTGCT | TATTTGGCAT | 1080 |
| TTTGTGGTAT | TGTTCTTCAT | AATGCTCAGC | TCTATGAGAC | TTCACTGCTG | GAGAACAAGA | 1140 |
| GAAATCAGGT | GCTGCTTGAC | CTTGCTAGTT | TAATTTTGA | AGAACAACAA | TCATTAGAAG | 1200 |
| TAATTTTGAA | GAAAATAGCT | GCCACTATTA | TCTCTTTCAT | GCAAGTGCAG | AAATGCACCA | 1260 |
| TTTTCATAGT | GGATGAAGAT | TGCTCCGATT | CTTTTCTAG | TGTGTTTCAC | ATGGAGTGTG | 1320 |
| AGGAATTAGA | AAAATCATCT | GATACATTAA | CAAGGGAACA | TGATGCAAAC | AAAATCAATT | 1380 |
| ACATGTATGC | TCAGTATGTC | AAAAATACTA | TGGAACCACT | TTATATCCCA | GATGTCAGTA | 1440 |
| AGGATAAAAG | ATTTCCCTGG | ACAACTGAAA | ATACAGGAAA | TGTAAACCAG | CAGTGCATTA | 1500 |
| GAAGTTTGCT | TTGTACACCT | ATAAAAAATG | GAAAGAAGAA | TAAAGTTATA | GGGGTTTGCC | 1560 |
| AACTTGTTAA | TAAGATGGAG | GAGAATACTG | GCAAGGTTAA | GCCTTTCAAC | CGAAATGACG | 1620 |
| AACAGTTTCT | GGAAGCTTTT | GTCATCTTTT | GTGGCTTGGG | GATCCAGAAC | ACGCAGATGT | 1680 |
| ATGAAGCAGT | GGAGAGAGCC | ATGGCCAAGC | AAATGGTCAC | ATTGGAGGTT | CTGTCGTATC | 1740 |
| ATGCTTCAGC | AGCAGAGGAA | GAAACAAGAG | AGCTACAGTC | GTTAGCGGCT | GCTGTGGTGC | 1800 |
| CATCTGCCCA | GACCCTTAAA | ATTACTGACT | TTAGCTTCAG | TGACTTTGAG | CTGTCTGATC | 1860 |
| TGGAAACAGC | ACTGTGTACA | ATTCGGATGT | TTACTGACCT | CAACCTTGTG | CAGAACTTCC | 1920 |
| AGATGAAACA | TGAGGTTCTT | TGCAGATGGA | TTTTAAGTGT | TAAGAAGAAT | TATCGGAAGA | 1980 |
| ATGTTGCCTA | TCATAATTGG | AGACATGCCT | TTAATACAGC | TCAGTGCATG | TTTGCTGCTC | 2040 |
| TAAAAGCAGG | CAAAATTCAG | | | | | 2060 |

(2) INFORMATION FOR SEQ ID NO:12:

(i) SEQUENCE CHARACTERISTICS:
 (A) LENGTH: 1982 base pairs
 (B) TYPE: nucleic acid ( C ) STRANDEDNESS: single
( D ) TOPOLOGY: linear ( i i ) MOLECULE TYPE: cDNA ( x i ) SEQUENCE DESCRIPTION: SEQ ID NO:12:

```
ACAAAATTTT CTTGCATATC CATGGACTGA TATCTGCTGA CCGCTATTCC CTGTTCCTTG        60
TCTGTGAAGA CAGCTCCAAT GACAAGTTTC TTATCAGCCG CCTCTTTGAT GTTGCTGAAG       120
GTTCAACACT GGAAGAAGTT TCAAATAACT GTATCCGCTT AGAATGGAAC AAAGGCATTG       180
TGGGACATGT GGCAGCGCTT GGTGAGCCCT GAACATCAA AGATGCATAT GAGGATCCTC        240
GGTTCAATGC AGAAGTTGAC CAAATTACAG GCTACAAGAC ACAAAGCATT CTTTGTATGC       300
CAATTAAGAA TCATAGGGAA GAGGTTGTTG GTGTAGCCCA GGCCATCAAC AAGAAATCAG       360
GAAACGGTGG GACATTTACT GAAAAGATG AAAAGGACTT TGCTGCTTAT TTGGCATTTT        420
GTGGTATTGT TCTTCATAAT GCTCAGCTCT ATGAGACTTC ACTGCTGGAG AACAAGAGAA       480
ATCAGGTGCT GCTTGACCTT GCTAGTTTAA TTTTTGAAGA ACAACAATCA TTAGAAGTAA       540
TTTTGAAGAA AATAGCTGCC ACTATTATCT CTTTCATGCA AGTGCAGAAA TGCACCATTT       600
TCATAGTGGA TGAAGATTGC TCCGATTCTT TTTCTAGTGT GTTCACATG GAGTGTGAGG        660
AATTAGAAAA ATCATCTGAT ACATTAACAA GGGAACATGA TGCAAACAAA ATCAATTACA       720
TGTATGCTCA GTATGTCAAA AATACTATGG AACCACTTAA TATCCCAGAT GTCAGTAAGG       780
ATAAAGATT TCCCTGGACA ACTGAAAATA CAGGAAATGT AAACCAGCAG TGCATTAGAA        840
GTTTGCTTTG TACACCTATA AAAAATGGAA AGAAGAATAA AGTTATAGGG GTTTGCCAAC       900
TTGTTAATAA GATGGAGGAG AATACTGGCA AGGTTAAGCC TTTCAACCGA ATGACGAAC        960
AGTTTCTGGA AGCTTTTGTC ATCTTTTGTG GCTTGGGGAT CCAGAACACG CAGATGTATG      1020
AAGCAGTGGA GAGAGCCATG GCCAAGCAAA TGGTCACATT GGAGGTTCTG TCGTATCATG      1080
CTTCAGCAGC AGAGGAAGAA ACAAGAGAGC TACAGTCGTT AGCGGCTGCT GTGGTGCCAT      1140
CTGCCCAGAC CCTTAAAATT ACTGACTTTA GCTTCAGTGA CTTGAGCTG TCTGATCTGG       1200
AAACAGCACT GTGTACAATT CGGATGTTTA CTGACCTCAA CCTTGTGCAG AACTTCCAGA      1260
TGAAACATGA GGTTCTTTGC AGATGGATTT TAAGTGTTAA GAAGAATTAT CGGAAGAATG      1320
TTGCCTATCA TAATTGGAGA CATGCCTTTA ATACAGCTCA GTGCATGTTT GCTGCTCTAA      1380
AAGCAGGCAA AATTCAGAAC AAGCTGACTG ACCTGGAGAT ACTTGCATTG CTGATTGCTG      1440
CACTAAGCCA CGATTTGGAT CACCGTGGTG TGAATAACTC TTACATACAG CGAAGTGAAC      1500
ATCCACTTGC CCAGCTTTAC TGCCATTCAA TCATGGAACA CCATCATTTT GACCAGTGCC      1560
TGATGATTCT TAATAGTCCA GGCAATCAGA TTCTCAGTGG CCTCTCCATT GAAGAATATA      1620
AGACCACGTT GAAATAATC AAGCAAGCTA TTTTAGCTAC AGACCTAGCA CTGTACATTA       1680
AGAGGCGAGG AGAATTTTTT GAACTTATAA GAAAAAATCA ATTCAATTTG GAAGATCCTC      1740
ATCAAAAGGA GTTGTTTTTG GCAATGCTGA TGACAGCTTG TGATCTTTCT GCAATTACAA      1800
AACCCTGGCC TATTCAACAA CGGATAGCAG AACTTGTAGC AACTGAATTT TTTGATCAAG      1860
GAGACAGAGA GAGAAAAGAA CTCAACATAG AACCCACTGA TCTAATGAAC AGGGAGAAGA      1920
AAAACAAAAT CCCAAGTATG CAAGTTGGGT TCATAGATGC CATCTGCTTG CAACTGTATG      1980
AG                                                                      1982
```

( 2 ) INFORMATION FOR SEQ ID NO:13:

( i ) SEQUENCE CHARACTERISTICS:
( A ) LENGTH: 18 base pairs (B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:13:

GCCACCAGAG AAATGGTC  18

(2) INFORMATION FOR SEQ ID NO:14:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:14:

ACAATGGGTC TAAGAGGC  18

(2) INFORMATION FOR SEQ ID NO:15:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:15:

TCAGTGCATG TTTGCTGC  18

(2) INFORMATION FOR SEQ ID NO:16:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:16:

TACAAACATG TTCATCAG  18

(2) INFORMATION FOR SEQ ID NO:17:

(i) SEQUENCE CHARACTERISTICS:
(A) LENGTH: 1107 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:17:

GAGACATGCC TTTAATACAG CTCAGTGCAT GTTTGCTGCT CTAAAAGCAG GCAAAATTCA  60
GAACAAGCTG ACTGACCTGG AGATACTTGC ATTGCTGATT GCTGCACTAA GCCACGATTT  120
GGATCACCGT GGTGTGAATA ACTCTTACAT ACAGCGAAGT GAACATCCAC TTGCCCAGCT  180
TTACTGCCAT TCAATCATGG AACACCATCA TTTTGACCAG TGCCTGATGA TTCTTAATAG  240
TCCAGGCAAT CAGATTCTCA GTGGCCTCTC CATTGAAGAA TATAAGACCA CGTTGAAAAT  300
AATCAAGCAA GCTATTTTAG CTACAGACCT AGCACTGTAC ATTAAGAGGC GAGGAGAATT  360

| | | | | | |
|---|---|---|---|---|---|
| TTTTGAACTT | ATAAGAAAAA | ATCAATTCAA | TTTGGAAGAT | CCTCATCAAA | AGGAGTTGTT | 420
| TTTGGCAATG | CTGATGACAG | CTTGTGATCT | TTCTGCAATT | ACAAAACCCT | GGCCTATTCA | 480
| ACAACGGATA | GCAGAACTTG | TAGCAACTGA | ATTTTTTGAT | CAAGGAGACA | GAGAGAGAAA | 540
| AGAACTCAAC | ATAGAACCCA | CTGATCTAAT | GAACAGGGAG | AAGAAAAACA | AAATCCCAAG | 600
| TATGCAAGTT | GGGTTCATAG | ATGCCATCTG | CTTGCAACTG | TATGAGGCCC | TGACCCACGT | 660
| GTCAGAGGAC | TGTTTCCCTT | TGCTAGATGG | CTGCAGAAAG | AACAGGCAGA | AATGGCAGGC | 720
| CCTTGCAGAA | CAGCAGGAGA | AGATGCTGAT | TAATGGGGAA | AGCGGCCAGG | CCAAGCGGAA | 780
| CTGAGTGGCC | TATTTCATGC | AGAGTTGAAG | TTTACAGAGA | TGGTGTGTTC | TGCAATATGC | 840
| CTAGTTTCTT | ACACACTGTC | TGTATAGTGT | CTGTATTTGG | TATATACTTT | GCCACTGCTG | 900
| TATTTTTATT | TTTGCACAAC | TTTTGAGAGT | ATAGCATGAA | TGTTTTAGA | GGACTATTAC | 960
| ATATTTTTG | TATATTTGTT | TTATGCTACT | GAACTGAAAG | GATCAACAAC | ATCCACTGTT | 1020
| AGCACATTGA | TAAAAGCATT | GTTTGTGATA | TTTCGTGTAC | TGCAAAGTGT | ATGCAGTATT | 1080
| CTTGCACTGA | GGTTTTTTTG | CTTGGGG | | | | 1107

( 2 ) INFORMATION FOR SEQ ID NO:18:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:18:

TTTGGAAGAT CCTCATCA  18

( 2 ) INFORMATION FOR SEQ ID NO:19:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:19:

ATGTCTCGAG TCAGTTCCGC TTGGCCTG  28

( 2 ) INFORMATION FOR SEQ ID NO:20:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:20:

TACAGAATTC TGACCATGGA GCGGGCCGGC  30

( 2 ) INFORMATION FOR SEQ ID NO:21:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:21:

CATTCTAAGC GGATACAG    18

( 2 ) INFORMATION FOR SEQ ID NO:22:

( i ) SEQUENCE CHARACTERISTICS:
      ( A ) LENGTH: 2645 base pairs
      ( B ) TYPE: nucleic acid
      ( C ) STRANDEDNESS: single
      ( D ) TOPOLOGY: linear ( i i ) MOLECULE TYPE: cDNA ( i x ) FEATURE:
      ( A ) NAME/KEY: CDS
      ( B ) LOCATION: 12..2636

( x i ) SEQUENCE DESCRIPTION: SEQ ID NO:22:

```
GAATTCTGAC C ATG GAG CGG GCC GGC CCC AGC TTC GGG CAG CAG CGA CAG        50
            Met Glu Arg Ala Gly Pro Ser Phe Gly Gln Gln Arg Gln
              1               5                  10

CAG CAG CAG CCC CAG CAG CAG AAG CAG CAG CAG AGG GAT CAG GAC TCG         98
Gln Gln Gln Pro Gln Gln Gln Lys Gln Gln Gln Arg Asp Gln Asp Ser
         15              20                  25

GTC GAA GCA TGG CTG GAC GAT CAC TGG GAC TTT ACC TTC TCA TAC TTT        146
Val Glu Ala Trp Leu Asp Asp His Trp Asp Phe Thr Phe Ser Tyr Phe
 30              35                  40                      45

GTT AGA AAA GCC ACC AGA GAA ATG GTC AAT GCA TGG TTT GCT GAG AGA        194
Val Arg Lys Ala Thr Arg Glu Met Val Asn Ala Trp Phe Ala Glu Arg
                 50                  55                  60

GTT CAC ACC ATC CCT GTG TGC AAG GAA GGT ATC AGA GGC CAC ACC GAA        242
Val His Thr Ile Pro Val Cys Lys Glu Gly Ile Arg Gly His Thr Glu
                 65                  70                  75

TCT TGC TCT TGT CCC TTG CAG CAG AGT CCT CGT GCA GAT AAC AGT GTC        290
Ser Cys Ser Cys Pro Leu Gln Gln Ser Pro Arg Ala Asp Asn Ser Val
             80                  85                  90

CCT GGA ACA CCA ACC AGG AAA ATC TCT GCC TCT GAA TTT GAC CGG CCT        338
Pro Gly Thr Pro Thr Arg Lys Ile Ser Ala Ser Glu Phe Asp Arg Pro
         95                 100                 105

CTT AGA CCC ATT GTT GTC AAG GAT TCT GAG GGA ACT GTG AGC TTC CTC        386
Leu Arg Pro Ile Val Val Lys Asp Ser Glu Gly Thr Val Ser Phe Leu
110                 115                 120                 125

TCT GAC TCA GAA AAG AAG GAA CAG ATG CCT CTA ACC CCT CCA AGG TTT        434
Ser Asp Ser Glu Lys Lys Glu Gln Met Pro Leu Thr Pro Pro Arg Phe
                130                 135                 140

GAT CAT GAT GAA GGG GAC CAG TGC TCA AGA CTC TTG GAA TTA GTG AAG        482
Asp His Asp Glu Gly Asp Gln Cys Ser Arg Leu Leu Glu Leu Val Lys
                145                 150                 155

GAT ATT TCT AGT CAT TTG GAT GTC ACA GCC TTA TGT CAC AAA ATT TTC        530
Asp Ile Ser Ser His Leu Asp Val Thr Ala Leu Cys His Lys Ile Phe
            160                 165                 170

TTG CAT ATC CAT GGA CTG ATA TCT GCT GAC CGC TAT TCC CTG TTC CTT        578
Leu His Ile His Gly Leu Ile Ser Ala Asp Arg Tyr Ser Leu Phe Leu
    175                 180                 185

GTC TGT GAA GAC AGC TCC AAT GAC AAG TTT CTT ATC AGC CGC CTC TTT        626
Val Cys Glu Asp Ser Ser Asn Asp Lys Phe Leu Ile Ser Arg Leu Phe
190                 195                 200                 205

GAT GTT GCT GAA GGT TCA ACA CTG GAA GAA GTT TCA AAT AAC TGT ATC        674
Asp Val Ala Glu Gly Ser Thr Leu Glu Glu Val Ser Asn Asn Cys Ile
                210                 215                 220

CGC TTA GAA TGG AAC AAA GGC ATT GTG GGA CAT GTG GCA GCG CTT GGT        722
```

```
                Arg Leu Glu Trp Asn Lys Gly Ile Val Gly His Val Ala Ala Leu Gly
                    225             230             235

GAG CCC TTG AAC ATC AAA GAT GCA TAT GAG GAT CCT CGG TTC AAT GCA            770
Glu Pro Leu Asn Ile Lys Asp Ala Tyr Glu Asp Pro Arg Phe Asn Ala
        240             245             250

GAA GTT GAC CAA ATT ACA GGC TAC AAG ACA CAA AGC ATT CTT TGT ATG            818
Glu Val Asp Gln Ile Thr Gly Tyr Lys Thr Gln Ser Ile Leu Cys Met
    255             260             265

CCA ATT AAG AAT CAT AGG GAA GAG GTT GTT GGT GTA GCC CAG GCC ATC            866
Pro Ile Lys Asn His Arg Glu Glu Val Val Gly Val Ala Gln Ala Ile
270             275             280             285

AAC AAG AAA TCA GGA AAC GGT GGG ACA TTT ACT GAA AAA GAT GAA AAG            914
Asn Lys Lys Ser Gly Asn Gly Gly Thr Phe Thr Glu Lys Asp Glu Lys
            290             295             300

GAC TTT GCT GCT TAT TTG GCA TTT TGT GGT ATT GTT CTT CAT AAT GCT            962
Asp Phe Ala Ala Tyr Leu Ala Phe Cys Gly Ile Val Leu His Asn Ala
                305             310             315

CAG CTC TAT GAG ACT TCA CTG CTG GAG AAC AAG AGA AAT CAG GTG CTG           1010
Gln Leu Tyr Glu Thr Ser Leu Leu Glu Asn Lys Arg Asn Gln Val Leu
        320             325             330

CTT GAC CTT GCT AGT TTA ATT TTT GAA GAA CAA CAA TCA TTA GAA GTA           1058
Leu Asp Leu Ala Ser Leu Ile Phe Glu Glu Gln Gln Ser Leu Glu Val
    335             340             345

ATT TTG AAG AAA ATA GCT GCC ACT ATT ATC TCT TTC ATG CAA GTG CAG           1106
Ile Leu Lys Lys Ile Ala Ala Thr Ile Ile Ser Phe Met Gln Val Gln
350             355             360             365

AAA TGC ACC ATT TTC ATA GTG GAT GAA GAT TGC TCC GAT TCT TTT TCT           1154
Lys Cys Thr Ile Phe Ile Val Asp Glu Asp Cys Ser Asp Ser Phe Ser
            370             375             380

AGT GTG TTT CAC ATG GAG TGT GAG GAA TTA GAA AAA TCA TCT GAT ACA           1202
Ser Val Phe His Met Glu Cys Glu Glu Leu Glu Lys Ser Ser Asp Thr
                385             390             395

TTA ACA AGG GAA CAT GAT GCA AAC AAA ATC AAT TAC ATG TAT GCT CAG           1250
Leu Thr Arg Glu His Asp Ala Asn Lys Ile Asn Tyr Met Tyr Ala Gln
        400             405             410

TAT GTC AAA AAT ACT ATG GAA CCA CTT AAT ATC CCA GAT GTC AGT AAG           1298
Tyr Val Lys Asn Thr Met Glu Pro Leu Asn Ile Pro Asp Val Ser Lys
    415             420             425

GAT AAA AGA TTT CCC TGG ACA ACT GAA AAT ACA GGA AAT GTA AAC CAG           1346
Asp Lys Arg Phe Pro Trp Thr Thr Glu Asn Thr Gly Asn Val Asn Gln
430             435             440             445

CAG TGC ATT AGA AGT TTG CTT TGT ACA CCT ATA AAA AAT GGA AAG AAG           1394
Gln Cys Ile Arg Ser Leu Leu Cys Thr Pro Ile Lys Asn Gly Lys Lys
            450             455             460

AAT AAA GTT ATA GGG GTT TGC CAA CTT GTT AAT AAG ATG GAG GAG AAT           1442
Asn Lys Val Ile Gly Val Cys Gln Leu Val Asn Lys Met Glu Glu Asn
                465             470             475

ACT GGC AAG GTT AAG CCT TTC AAC CGA AAT GAC GAA CAG TTT CTG GAA           1490
Thr Gly Lys Val Lys Pro Phe Asn Arg Asn Asp Glu Gln Phe Leu Glu
        480             485             490

GCT TTT GTC ATC TTT TGT GGC TTG GGG ATC CAG AAC ACG CAG ATG TAT           1538
Ala Phe Val Ile Phe Cys Gly Leu Gly Ile Gln Asn Thr Gln Met Tyr
    495             500             505

GAA GCA GTG GAG AGA GCC ATG GCC AAG CAA ATG GTC ACA TTG GAG GTT           1586
Glu Ala Val Glu Arg Ala Met Ala Lys Gln Met Val Thr Leu Glu Val
510             515             520             525

CTG TCG TAT CAT GCT TCA GCA GCA GAG GAA GAA ACA AGA GAG CTA CAG           1634
Leu Ser Tyr His Ala Ser Ala Ala Glu Glu Glu Thr Arg Glu Leu Gln
            530             535             540

TCG TTA GCG GCT GCT GTG GTG CCA TCT GCC CAG ACC CTT AAA ATT ACT           1682
```

| | | | | | | | | | | | | | | | |
|---|---|---|---|---|---|---|---|---|---|---|---|---|---|---|---|
| Ser | Leu | Ala | Ala | Ala | Val | Val | Pro | Ser | Ala | Gln | Thr | Leu | Lys | Ile | Thr |
| | | | 545 | | | | | 550 | | | | | 555 | | |

```
GAC TTT AGC TTC AGT GAC TTT GAG CTG TCT GAT CTG GAA ACA GCA CTG       1730
Asp Phe Ser Phe Ser Asp Phe Glu Leu Ser Asp Leu Glu Thr Ala Leu
        560                 565                 570

TGT ACA ATT CGG ATG TTT ACT GAC CTC AAC CTT GTG CAG AAC TTC CAG       1778
Cys Thr Ile Arg Met Phe Thr Asp Leu Asn Leu Val Gln Asn Phe Gln
575                 580                 585

ATG AAA CAT GAG GTT CTT TGC AGA TGG ATT TTA AGT GTT AAG AAG AAT       1826
Met Lys His Glu Val Leu Cys Arg Trp Ile Leu Ser Val Lys Lys Asn
590                 595                 600                 605

TAT CGG AAG AAT GTT GCC TAT CAT AAT TGG AGA CAT GCC TTT AAT ACA       1874
Tyr Arg Lys Asn Val Ala Tyr His Asn Trp Arg His Ala Phe Asn Thr
                610                 615                 620

GCT CAG TGC ATG TTT GCT GCT CTA AAA GCA GGC AAA ATT CAG AAC AAG       1922
Ala Gln Cys Met Phe Ala Ala Leu Lys Ala Gly Lys Ile Gln Asn Lys
            625                 630                 635

CTG ACT GAC CTG GAG ATA CTT GCA TTG CTG ATT GCT GCA CTA AGC CAC       1970
Leu Thr Asp Leu Glu Ile Leu Ala Leu Leu Ile Ala Ala Leu Ser His
        640                 645                 650

GAT TTG GAT CAC CGT GGT GTG AAT AAC TCT TAC ATA CAG CGA AGT GAA       2018
Asp Leu Asp His Arg Gly Val Asn Asn Ser Tyr Ile Gln Arg Ser Glu
655                 660                 665

CAT CCA CTT GCC CAG CTT TAC TGC CAT TCA ATC ATG GAA CAC CAT CAT       2066
His Pro Leu Ala Gln Leu Tyr Cys His Ser Ile Met Glu His His His
670                 675                 680                 685

TTT GAC CAG TGC CTG ATG ATT CTT AAT AGT CCA GGC AAT CAG ATT CTC       2114
Phe Asp Gln Cys Leu Met Ile Leu Asn Ser Pro Gly Asn Gln Ile Leu
                690                 695                 700

AGT GGC CTC TCC ATT GAA GAA TAT AAG ACC ACG TTG AAA ATA ATC AAG       2162
Ser Gly Leu Ser Ile Glu Glu Tyr Lys Thr Thr Leu Lys Ile Ile Lys
            705                 710                 715

CAA GCT ATT TTA GCT ACA GAC CTA GCA CTG TAC ATT AAG AGG CGA GGA       2210
Gln Ala Ile Leu Ala Thr Asp Leu Ala Leu Tyr Ile Lys Arg Arg Gly
        720                 725                 730

GAA TTT TTT GAA CTT ATA AGA AAA AAT CAA TTC AAT TTG GAA GAT CCT       2258
Glu Phe Phe Glu Leu Ile Arg Lys Asn Gln Phe Asn Leu Glu Asp Pro
735                 740                 745

CAT CAA AAG GAG TTG TTT TTG GCA ATG CTG ATG ACA GCT TGT GAT CTT       2306
His Gln Lys Glu Leu Phe Leu Ala Met Leu Met Thr Ala Cys Asp Leu
750                 755                 760                 765

TCT GCA ATT ACA AAA CCC TGG CCT ATT CAA CAA CGG ATA GCA GAA CTT       2354
Ser Ala Ile Thr Lys Pro Trp Pro Ile Gln Gln Arg Ile Ala Glu Leu
                770                 775                 780

GTA GCA ACT GAA TTT TTT GAT CAA GGA GAC AGA GAG AGA AAA GAA CTC       2402
Val Ala Thr Glu Phe Phe Asp Gln Gly Asp Arg Glu Arg Lys Glu Leu
            785                 790                 795

AAC ATA GAA CCC ACT GAT CTA ATG AAC AGG GAG AAG AAA AAC AAA ATC       2450
Asn Ile Glu Pro Thr Asp Leu Met Asn Arg Glu Lys Lys Asn Lys Ile
        800                 805                 810

CCA AGT ATG CAA GTT GGG TTC ATA GAT GCC ATC TGC TTG CAA CTG TAT       2498
Pro Ser Met Gln Val Gly Phe Ile Asp Ala Ile Cys Leu Gln Leu Tyr
815                 820                 825

GAG GCC CTG ACC CAC GTG TCA GAG GAC TGT TTC CCT TTG CTA GAT GGC       2546
Glu Ala Leu Thr His Val Ser Glu Asp Cys Phe Pro Leu Leu Asp Gly
830                 835                 840                 845

TGC AGA AAG AAC AGG CAG AAA TGG CAG GCC CTT GCA GAA CAG CAG GAG       2594
Cys Arg Lys Asn Arg Gln Lys Trp Gln Ala Leu Ala Glu Gln Gln Glu
                850                 855                 860

AAG ATG CTG ATT AAT GGG GAA AGC GGC CAG GCC AAG CGG AAC                2636
```

```
Lys  Met  Leu  Ile  Asn  Gly  Glu  Ser  Gly  Gln  Ala  Lys  Arg  Asn
               865                 870                      875

TGACTCGAG                                                                                    2645
```

(2) INFORMATION FOR SEQ ID NO:23:

(i) SEQUENCE CHARACTERISTICS:
       (A) LENGTH: 875 amino acids
       (B) TYPE: amino acid
       (D) TOPOLOGY: linear (ii) MOLECULE TYPE: protein (xi) SEQUENCE DESCRIPTION: SEQ ID NO:23:

```
Met  Glu  Arg  Ala  Gly  Pro  Ser  Phe  Gly  Gln  Arg  Gln  Gln  Gln  Gln
 1                  5                   10                       15

Pro  Gln  Gln  Gln  Lys  Gln  Gln  Gln  Arg  Asp  Gln  Asp  Ser  Val  Glu  Ala
                20                  25                       30

Trp  Leu  Asp  Asp  His  Trp  Asp  Phe  Thr  Phe  Ser  Tyr  Phe  Val  Arg  Lys
               35                  40                       45

Ala  Thr  Arg  Glu  Met  Val  Asn  Ala  Trp  Phe  Ala  Glu  Arg  Val  His  Thr
      50                  55                       60

Ile  Pro  Val  Cys  Lys  Glu  Gly  Ile  Arg  Gly  His  Thr  Glu  Ser  Cys  Ser
 65                  70                       75                       80

Cys  Pro  Leu  Gln  Gln  Ser  Pro  Arg  Ala  Asp  Asn  Ser  Val  Pro  Gly  Thr
                85                  90                       95

Pro  Thr  Arg  Lys  Ile  Ser  Ala  Ser  Glu  Phe  Asp  Arg  Pro  Leu  Arg  Pro
               100                 105                      110

Ile  Val  Val  Lys  Asp  Ser  Glu  Gly  Thr  Val  Ser  Phe  Leu  Ser  Asp  Ser
               115                 120                      125

Glu  Lys  Lys  Glu  Gln  Met  Pro  Leu  Thr  Pro  Pro  Arg  Phe  Asp  His  Asp
130                 135                      140

Glu  Gly  Asp  Gln  Cys  Ser  Arg  Leu  Leu  Glu  Leu  Val  Lys  Asp  Ile  Ser
145                 150                      155                      160

Ser  His  Leu  Asp  Val  Thr  Ala  Leu  Cys  His  Lys  Ile  Phe  Leu  His  Ile
               165                 170                      175

His  Gly  Leu  Ile  Ser  Ala  Asp  Arg  Tyr  Ser  Leu  Phe  Leu  Val  Cys  Glu
               180                 185                      190

Asp  Ser  Ser  Asn  Asp  Lys  Phe  Leu  Ile  Ser  Arg  Leu  Phe  Asp  Val  Ala
          195                 200                      205

Glu  Gly  Ser  Thr  Leu  Glu  Glu  Val  Ser  Asn  Asn  Cys  Ile  Arg  Leu  Glu
          210                 215                      220

Trp  Asn  Lys  Gly  Ile  Val  Gly  His  Val  Ala  Ala  Leu  Gly  Glu  Pro  Leu
225                 230                      235                      240

Asn  Ile  Lys  Asp  Ala  Tyr  Glu  Asp  Pro  Arg  Phe  Asn  Ala  Glu  Val  Asp
                245                 250                      255

Gln  Ile  Thr  Gly  Tyr  Lys  Thr  Gln  Ser  Ile  Leu  Cys  Met  Pro  Ile  Lys
               260                 265                      270

Asn  His  Arg  Glu  Glu  Val  Val  Gly  Val  Ala  Gln  Ala  Ile  Asn  Lys  Lys
          275                 280                      285

Ser  Gly  Asn  Gly  Gly  Thr  Phe  Thr  Glu  Lys  Asp  Glu  Lys  Asp  Phe  Ala
          290                 295                      300

Ala  Tyr  Leu  Ala  Phe  Cys  Gly  Ile  Val  Leu  His  Asn  Ala  Gln  Leu  Tyr
305                 310                      315                      320

Glu  Thr  Ser  Leu  Leu  Glu  Asn  Lys  Arg  Asn  Gln  Val  Leu  Leu  Asp  Leu
               325                 330                      335
```

```
Ala  Ser  Leu  Ile  Phe  Glu  Glu  Gln  Ser  Leu  Glu  Val  Ile  Leu  Lys
               340                      345                    350

Lys  Ile  Ala  Ala  Thr  Ile  Ile  Ser  Phe  Met  Gln  Val  Gln  Lys  Cys  Thr
          355                      360                    365

Ile  Phe  Ile  Val  Asp  Glu  Asp  Cys  Ser  Asp  Ser  Phe  Ser  Ser  Val  Phe
          370                 375                    380

His  Met  Glu  Cys  Glu  Glu  Leu  Glu  Lys  Ser  Ser  Asp  Thr  Leu  Thr  Arg
385                      390                    395                         400

Glu  His  Asp  Ala  Asn  Lys  Ile  Asn  Tyr  Met  Tyr  Ala  Gln  Tyr  Val  Lys
                405                      410                         415

Asn  Thr  Met  Glu  Pro  Leu  Asn  Ile  Pro  Asp  Val  Ser  Lys  Asp  Lys  Arg
               420                      425                    430

Phe  Pro  Trp  Thr  Thr  Glu  Asn  Thr  Gly  Asn  Val  Asn  Gln  Gln  Cys  Ile
          435                      440                         445

Arg  Ser  Leu  Leu  Cys  Thr  Pro  Ile  Lys  Asn  Gly  Lys  Lys  Asn  Lys  Val
     450                      455                    460

Ile  Gly  Val  Cys  Gln  Leu  Val  Asn  Lys  Met  Glu  Glu  Asn  Thr  Gly  Lys
465                      470                    475                         480

Val  Lys  Pro  Phe  Asn  Arg  Asn  Asp  Glu  Gln  Phe  Leu  Glu  Ala  Phe  Val
               485                      490                         495

Ile  Phe  Cys  Gly  Leu  Gly  Ile  Gln  Asn  Thr  Gln  Met  Tyr  Glu  Ala  Val
               500                      505                         510

Glu  Arg  Ala  Met  Ala  Lys  Gln  Met  Val  Thr  Leu  Glu  Val  Leu  Ser  Tyr
          515                      520                    525

His  Ala  Ser  Ala  Ala  Glu  Glu  Glu  Thr  Arg  Glu  Leu  Gln  Ser  Leu  Ala
     530                      535                    540

Ala  Ala  Val  Val  Pro  Ser  Ala  Gln  Thr  Leu  Lys  Ile  Thr  Asp  Phe  Ser
545                      550                    555                         560

Phe  Ser  Asp  Phe  Glu  Leu  Ser  Asp  Leu  Glu  Thr  Ala  Leu  Cys  Thr  Ile
               565                      570                         575

Arg  Met  Phe  Thr  Asp  Leu  Asn  Leu  Val  Gln  Asn  Phe  Gln  Met  Lys  His
               580                      585                    590

Glu  Val  Leu  Cys  Arg  Trp  Ile  Leu  Ser  Val  Lys  Lys  Asn  Tyr  Arg  Lys
          595                      600                    605

Asn  Val  Ala  Tyr  His  Asn  Trp  Arg  His  Ala  Phe  Asn  Thr  Ala  Gln  Cys
610                      615                         620

Met  Phe  Ala  Ala  Leu  Lys  Ala  Gly  Lys  Ile  Gln  Asn  Lys  Leu  Thr  Asp
625                      630                      635                        640

Leu  Glu  Ile  Leu  Ala  Leu  Leu  Ile  Ala  Ala  Leu  Ser  His  Asp  Leu  Asp
                    645                      650                    655

His  Arg  Gly  Val  Asn  Asn  Ser  Tyr  Ile  Gln  Arg  Ser  Glu  His  Pro  Leu
               660                      665                    670

Ala  Gln  Leu  Tyr  Cys  His  Ser  Ile  Met  Glu  His  His  His  Phe  Asp  Gln
          675                      680                    685

Cys  Leu  Met  Ile  Leu  Asn  Ser  Pro  Gly  Asn  Gln  Ile  Leu  Ser  Gly  Leu
          690                      695                    700

Ser  Ile  Glu  Glu  Tyr  Lys  Thr  Thr  Leu  Lys  Ile  Ile  Lys  Gln  Ala  Ile
705                      710                      715                        720

Leu  Ala  Thr  Asp  Leu  Ala  Leu  Tyr  Ile  Lys  Arg  Arg  Gly  Glu  Phe  Phe
               725                      730                         735

Glu  Leu  Ile  Arg  Lys  Asn  Gln  Phe  Asn  Leu  Glu  Asp  Pro  His  Gln  Lys
               740                      745                    750

Glu  Leu  Phe  Leu  Ala  Met  Leu  Met  Thr  Ala  Cys  Asp  Leu  Ser  Ala  Ile
          755                      760                    765
```

-continued

| | | | | | | | | | | | | | | |
|---|---|---|---|---|---|---|---|---|---|---|---|---|---|---|
| Thr | Lys 770 | Pro | Trp | Pro | Ile | Gln 775 | Gln | Arg | Ile | Ala | Glu 780 | Leu | Val | Ala | Thr |
| Glu 785 | Phe | Phe | Asp | Gln 790 | Gly | Asp | Arg | Glu | Arg | Lys 795 | Glu | Leu | Asn | Ile | Glu 800 |
| Pro | Thr | Asp | Leu | Met 805 | Asn | Arg | Glu | Lys | Lys 810 | Asn | Lys | Ile | Pro | Ser 815 | Met |
| Gln | Val | Gly | Phe 820 | Ile | Asp | Ala | Ile | Cys 825 | Leu | Gln | Leu | Tyr | Glu 830 | Ala | Leu |
| Thr | His | Val 835 | Ser | Glu | Asp | Cys | Phe 840 | Pro | Leu | Leu | Asp | Gly 845 | Cys | Arg | Lys |
| Asn | Arg 850 | Gln | Lys | Trp | Gln | Ala 855 | Leu | Ala | Glu | Gln | Gln 860 | Glu | Lys | Met | Leu |
| Ile 865 | Asn | Gly | Glu | Ser | Gly 870 | Gln | Ala | Lys | Arg | Asn 875 | | | | | |